US011179271B2

(12) United States Patent
Baschnagel

(10) Patent No.: US 11,179,271 B2
(45) Date of Patent: Nov. 23, 2021

(54) DEFORMABLE THERMAL PACK

(71) Applicant: Robert Baschnagel, Garden City, NY (US)

(72) Inventor: Robert Baschnagel, Garden City, NY (US)

(73) Assignee: NYCE INNOVATIONS, LLC., Canton, MA (US)

(*) Notice: Subject to any disclaimer, the term of this patent is extended or adjusted under 35 U.S.C. 154(b) by 37 days.

(21) Appl. No.: 16/379,221

(22) Filed: Apr. 9, 2019

(65) Prior Publication Data
US 2019/0298569 A1 Oct. 3, 2019

Related U.S. Application Data

(63) Continuation-in-part of application No. 16/034,388, filed on Jul. 13, 2018.

(60) Provisional application No. 62/604,611, filed on Jul. 14, 2017.

(51) Int. Cl.
A61F 7/02 (2006.01)
A61F 7/00 (2006.01)

(52) U.S. Cl.
CPC .......... *A61F 7/02* (2013.01); *A61F 2007/003* (2013.01); *A61F 2007/0039* (2013.01); *A61F 2007/023* (2013.01); *A61F 2007/0279* (2013.01)

(58) Field of Classification Search
CPC .................. A61F 7/02; A61F 2007/023; A61F 2007/0039; A61F 2007/003; A61F 2007/0279; A61F 2007/0029; A61F 2007/0225; A61F 2007/0228

USPC .......................................................... 607/114
See application file for complete search history.

(56) References Cited

U.S. PATENT DOCUMENTS

| 5,395,399 | A | 3/1995 | Rosenwald |
| 5,716,388 | A * | 2/1998 | Petelle ...................... A61F 7/02 126/204 |
| 5,727,544 | A | 3/1998 | Miura |
| 7,060,086 | B2 | 6/2006 | Wilson et al. |
| 8,603,151 | B2 | 12/2013 | Latham |
| 2001/0051820 | A1 | 12/2001 | Rich |
| 2004/0167456 | A1 | 8/2004 | Kingsford et al. |
| 2004/0244412 | A1 | 12/2004 | Trinh et al. |

(Continued)

OTHER PUBLICATIONS

International Search Report together with the Written Opinion from related International Application No. PCT/US2019/040917 dated Nov. 15, 2019.

*Primary Examiner* — Linda C Dvorak
*Assistant Examiner* — Nils A Potter
(74) *Attorney, Agent, or Firm* — Scully, Scott, Murphy & Presser, P.C.

(57) ABSTRACT

Thermal packs including: a pouch containing a thermal source; and a bendable and deformable support attached to or disposed within the pouch, the support configured such that the pouch is deformed into a shape matching a contour of a body part and the pouch is maintained in the shape while applied to the body part by the support, where the support includes members, each of which having a cup at a first end and a ball at a second end, the ball of one of members being rotatably fitted within the cup of an adjacent one of the members; one or more wires encased in a casing or an loop or hook fastener such that a flap, having an other of the hook or loop fastener, extended from the pouch is folded over the support to retain the support adjacent to the pouch.

5 Claims, 32 Drawing Sheets

(56) References Cited

U.S. PATENT DOCUMENTS

| | | | |
|---|---|---|---|
| 2005/0261755 A1* | 11/2005 | Bacino | A61F 7/02 607/114 |
| 2006/0004427 A1 | 1/2006 | Wilson et al. | |
| 2006/0081000 A1 | 4/2006 | Trinh et al. | |
| 2007/0156213 A1* | 7/2007 | Friedensohn | A61F 7/03 607/114 |
| 2007/0256679 A1* | 11/2007 | Yim | A61F 7/034 126/263.02 |
| 2008/0140166 A1 | 6/2008 | Von Hoffman et al. | |
| 2008/0312722 A1 | 12/2008 | Wang | |
| 2009/0205106 A1 | 8/2009 | Sohn | |
| 2011/0093050 A1 | 4/2011 | Damkoehler | |
| 2016/0022480 A1 | 1/2016 | Biser et al. | |
| 2017/0209329 A1 | 7/2017 | Ishibashi et al. | |
| 2018/0243127 A1* | 8/2018 | Chavarry | A61F 7/02 |

\* cited by examiner

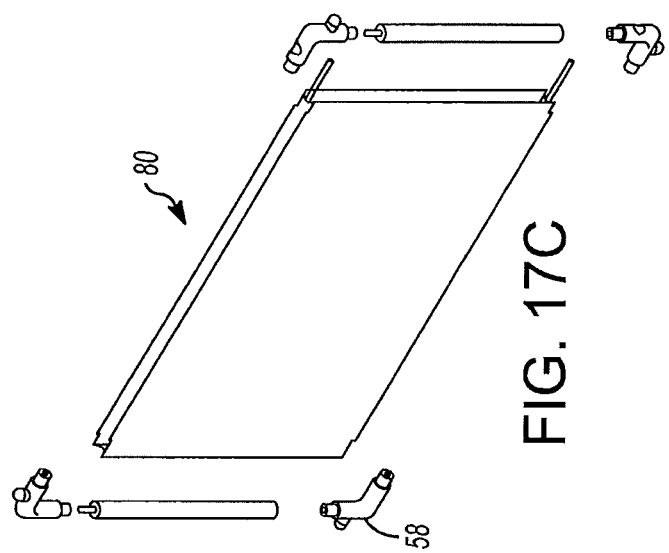
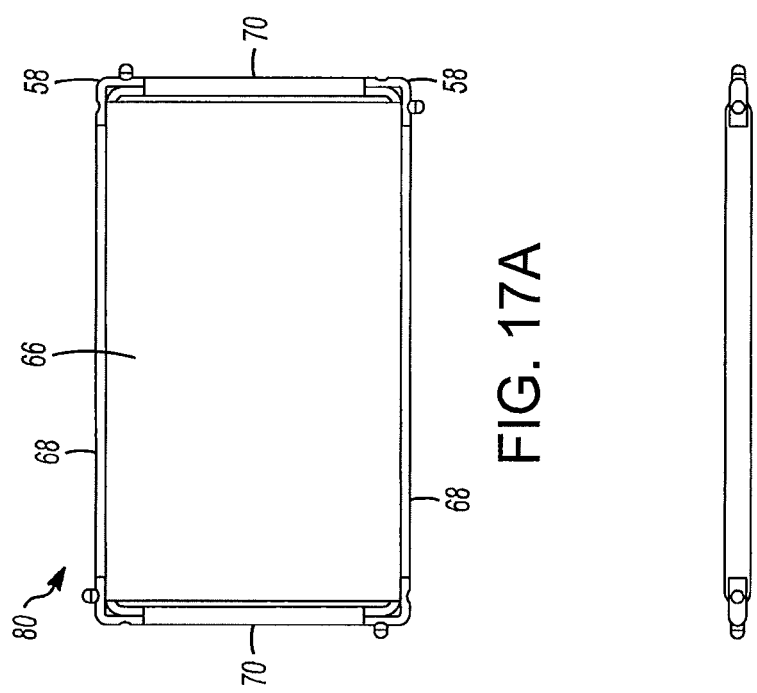

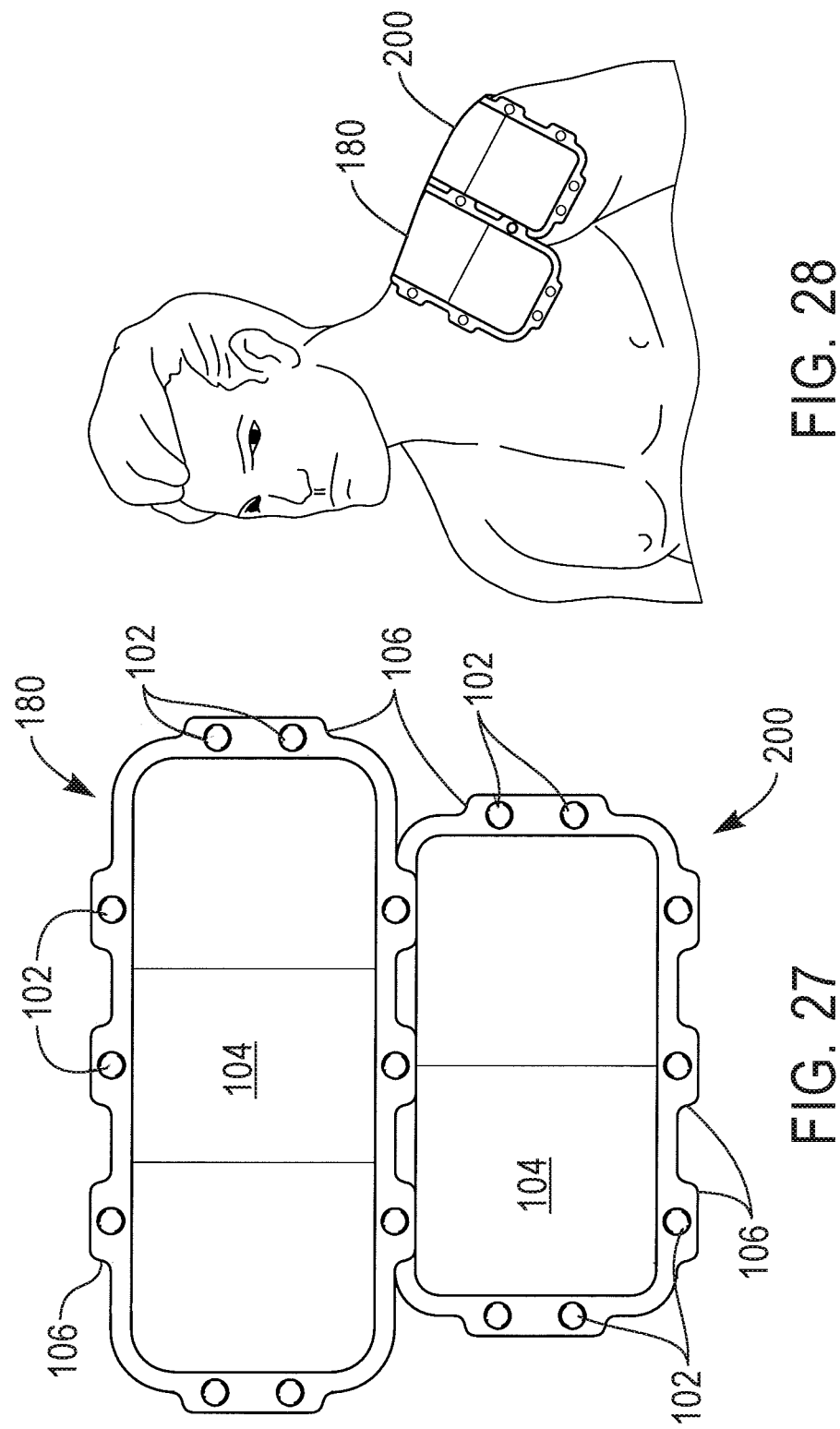

DEFORMABLE THERMAL PACK

CROSS REFERENCES TO RELATED APPLICATIONS

The present application is a Continuation-In-Part Application of U.S. application Ser. No. 16/034,388 filed on Jul. 13, 2018, which claims priority to provisional application 62/604,611 filed on Jul. 14, 2017 by the present inventor and entitled "A Thermal Treatment Pack".

BACKGROUND

Field

The present disclosure relates generally to treatment by applied temperature controlled materials, and, in particular, relates the treatment of pain or soreness, and, in greater particularity, relates to thermal treatment of pain or soreness by applied hot or cold packs.

Numerous types of ice packs and heat packs use straps for holding the packs to the body.

Further, many devices are shown in issued patents and patent applications publications such as the following: US Patent Application Pub. 2001/0051820 shows thermal treatment packs and the retainers for such. These are highly configurable with the use of cloth strips with fasteners. US Patent Application Pub. 2004/0167456 shows a medical wrap about an ankle using hook and loop. Ice or heat packs may be placed thereunder. US Patent Application Pub. 2004/0244412 shows a pouch for ice bags that is attached to clothing by safety pins. US Patent Application Pub. 2001/0051820 shows a pouch with adhesive tabs for attachment. US Patent Application Pub. 2006/0004427 shows a cylindrical tubular body of flexible material with a temperature retaining material therein that can be used on an arm or leg, but not a shoulder. US Patent Application Pub. 2006/0081000 shows a self-adhesive ice bag device pouch. US Patent Application Pub. 2008/0140166 shows a thermal pack with modules inside. One version is tubular. US Patent Application Pub. 2009/0205106 shows a tubular wrist band with elastic bands on the edges, but it does not provide for heating or cooling but for absorbing water on the wrist. US Patent Application Pub. 2011/0093050 shows a thermal wrap with a pouch for foot use. The wrap is held in place by Velcro straps. U.S. Pat. No. 5,395,399 shows a thermal wrap with a pouch for thermal material and is held in place by an elastic cloth. U.S. Pat. No. 7,060,086 shows a tubular thermal pack for use on hands and legs. U.S. Pat. No. 8,603,151 shows a cooling device for application to body parts having an external thermal source and is held in place by straps. All of these references are incorporated by reference.

Thus, there is a need for a more convenient device to threat pain or soreness.

SUMMARY

The present embodiments provide a flexible device for providing a source of thermal energy for treating pain or soreness in an arm, leg or shoulder.

A thermal pack may be applied to the body on an arm or leg or shoulder. A pouch for holding a thermal pack or being the thermal pack itself is held between parallel deformable, bendable rods that remain in that position to which bent until removed or adjusted. The rods may be on all four sides. The pack is generally rectangularly shaped with rounded corners, but other shapes may be considered. One end may be open and sealed by Velcro® after the appropriate thermal source whether a cooling source or heating source is placed therein, but the pouch may also hold a hot/cold therapy solution. The pouch may be an ice pack. If the source is the pouch, it is sold as a unit. The pack may come in various sizes for an arm, leg or shoulder. Additional features may be added to the pouch such as handles to aid in applying the pack. In general, the pack is held against the body part, i.e., wrist, and then bent around the wrist forming a "loosely" fitting cuff. This would be also done on the shoulder since the bendable rods will remain bent. The embodiments are directed at a person normally at rest and not contemplated for a person actively moving.

In another embodiment, a gel pack being either a cold pack or a heat pack, is fixedly attached to the flexible rods and may be used also to keep foods warm or cold, for example.

It is an object to provide a pack using thermal energy to treat pain or soreness;

It is another object to provide a pack being either hot or cold in this treatment;

It is a further object to provide a flexible thermal pack that loosely grips the body part and remains there while the body remains inactive;

It is still a further object to provide thermal pack whose shape is controlled by flexible and deformable rods;

It is still another object to provide a thermal treatment pack that does not require the use of straps;

It is still another object to provide hot/cold therapy packs for active people such as baby boomers or elderly who have a limited range of motion, or for people who are out of shape where the bendable rods may be tightened for greater compression.

It is still another object to provide a thermal treatment pack that is self-contained that can be temperature adjusted by cooling or heating the whole pack.

These and other objects, features, and advantages of the present invention will become more readily apparent from the attached drawings and the detailed description of the preferred embodiments, which follow.

BRIEF DESCRIPTION OF THE DRAWINGS

FIG. 17A shows by top view the thermal treatment pack;

FIG. 17B shows a side view of the pack of FIG. 17A;

FIG. 17C shows the thermal source with edge brackets bonded to the flexible rods thereabout with corner connectors for the flexible rods;

FIG. 27 illustrates a configuration of two thermal packs connected together;

FIG. 28 illustrates the two thermal packs of FIG. 27 used on a shoulder region of a user;

Like reference numerals refer to like parts throughout the several views of the drawings.

DETAILED DESCRIPTION

In general, a thermal treatment pack is applied to the body on an arm or leg or shoulder. A pouch for holding a thermal pack or being the thermal pack itself is held between parallel deformable, bendable rods that remain in that position to which bent. The rods may be on all four sides. The pack is generally rectangularly shaped with rounded corners, but other shapes may be considered. One end may be open and sealed by Velcro® after the appropriate thermal source whether a cooling source or heating source, but the pouch may also hold a hot/cold therapy solution. The pouch may be an ice pack. If the source is the pouch, it is sold as a unit. The pack may come in various sizes for an arm, leg or shoulder. Additional features may be added to the pouch such as handles to aid in applying the pack. In general, the pack is held against the body part, i.e., wrist, and then bent around the wrist forming a "loosely" fitting cuff. This would be also done on the shoulder since the bendable rods will remain bent. The invention is directed at a person normally at rest and not contemplated for a person actively moving. In another embodiment of the present invention, a gel pack being either a cold pack or a heat pack, is fixedly attached to the flexible rod and may be used also to keep foods warm or cold.

Figure 1:
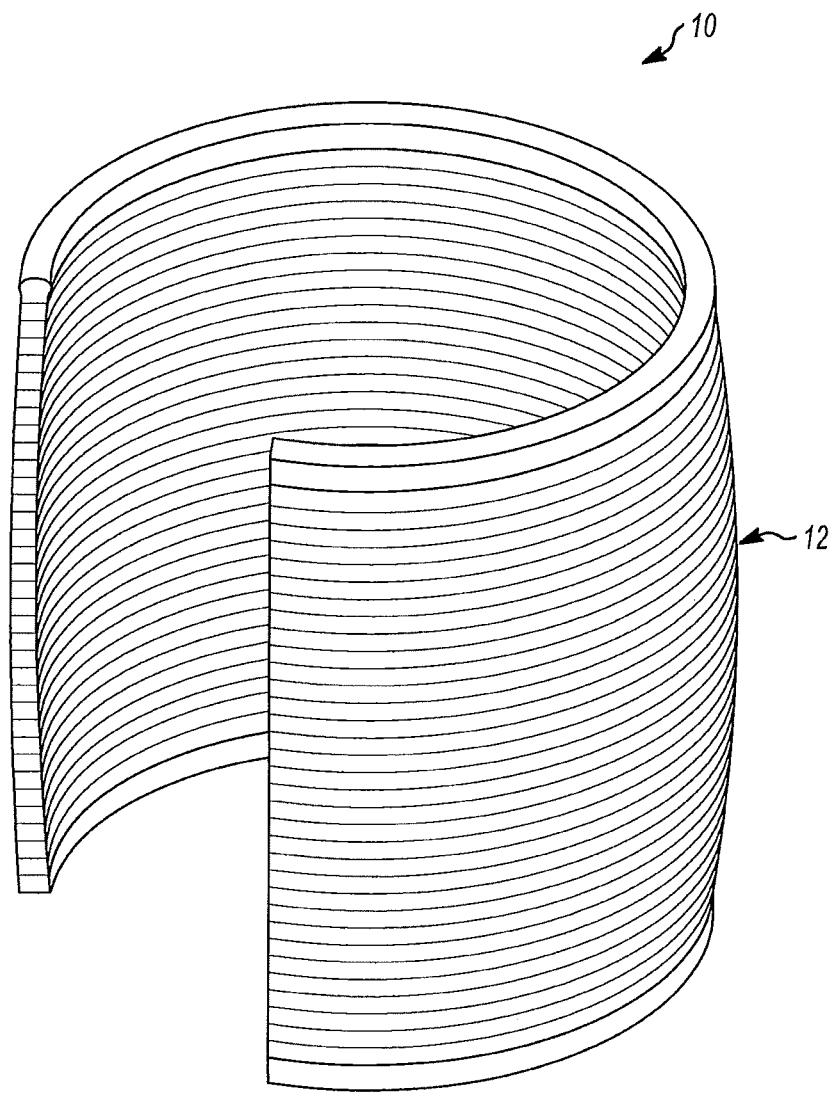
FIG. 1 is a perspective view of a thermal treatment pack formed into a cuff.
Figure 2:
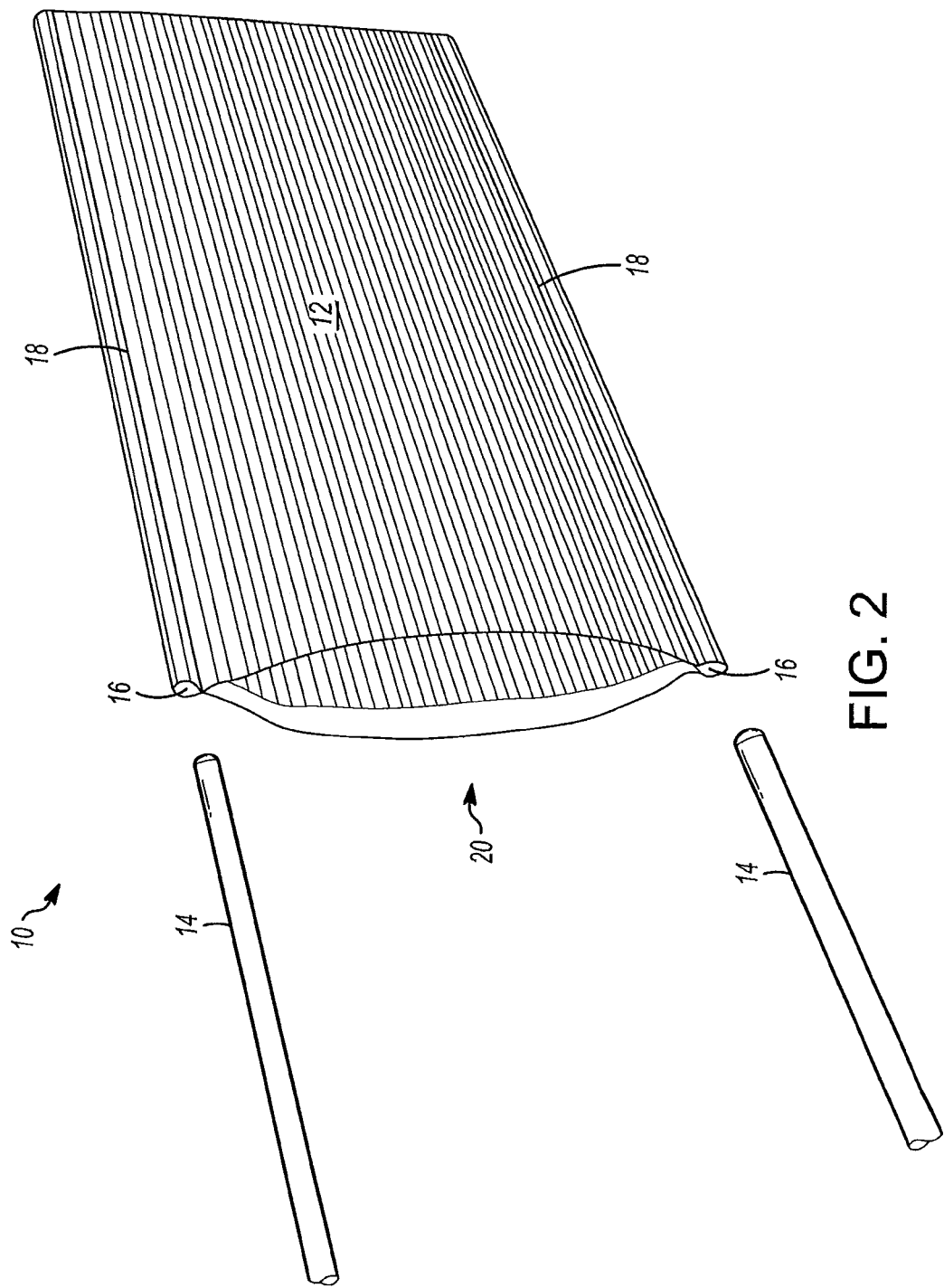
FIG. 2 is a perspective view showing the thermal treatment pack before the insertion of the flexible rods therein and before the insertion of a thermal source in a pouch.

FIG. 1 shows a deformable thermal treatment pack 10 that can be applied to the body such as at a leg, arm and even a shoulder with a thermal source or pouch 12 therein. The pack 10 is bent like a cuff and will remain in that shape since deformable rods are placed thereabout. See FIGS. 7, 10 and 11. In FIG. 2, the pouch 12 is held between two parallel deformable, bendable rods 14 that are enclosed in cylindrical sleeves 16 as shown in FIGS. 2 to 6. These rods provide a support frame for the pouch. The bendable rods 14 form a support frame 17 about the pouch 12. The sleeves 16 are made by stitching away from the pouch edges 18 an appropriate distance inward. Other conventional means such as gluing or heat bonding can be used to form the sleeves depending on the materials. The pack 10 is generally rectangularly shaped but other shapes may be used. It may be about 2 to 4 inches on a short edge and 4 to 6 inches on a long edge. One end 20 may be open and sealed by Velcro™ after the appropriate thermal source 22, FIG. 5, whether a cooling source or heating source is inserted into the pouch 10.

Figure 7:
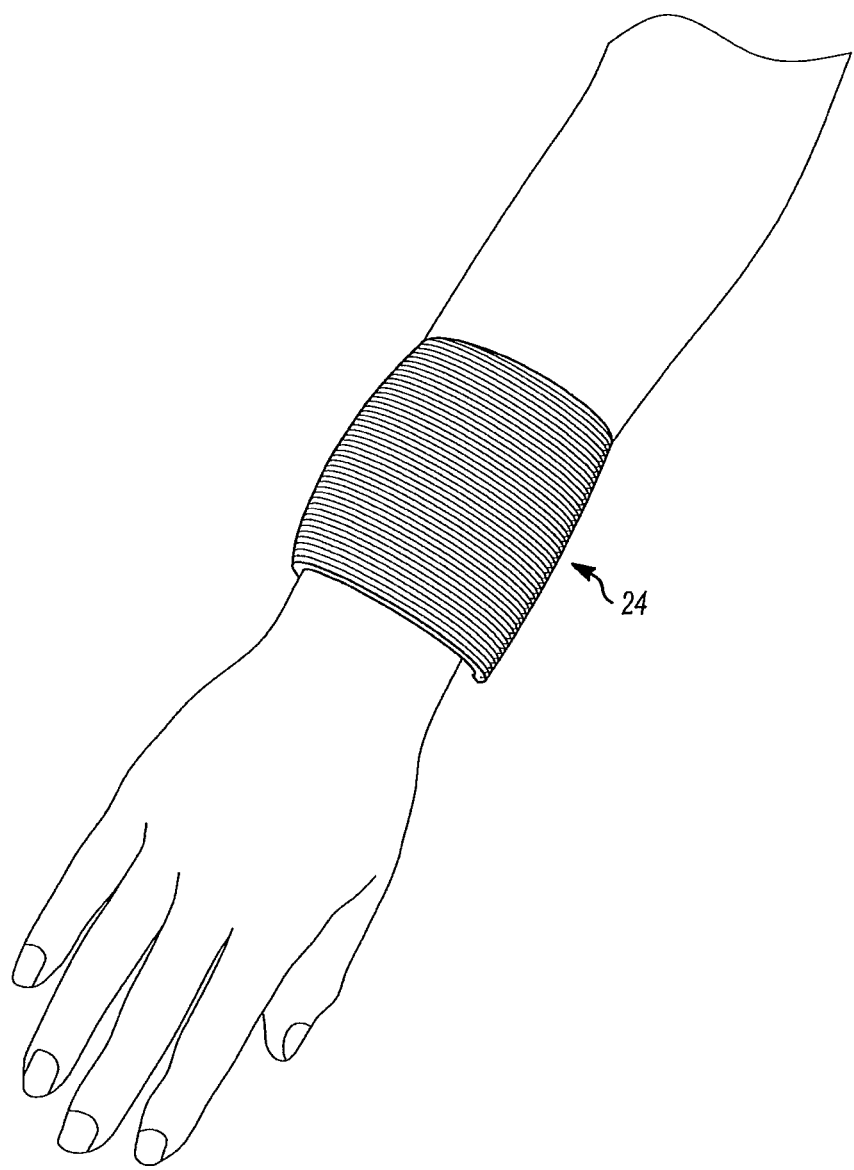
FIG. 7 shows the thermal treatment pack formed into a cuff and placed about a wrist.

In another embodiment, the appropriate thermal source whether an ice pack or hot/cold therapy solution may already be sealed in the pouch and sold as a unit. The walls of the pack 10 may be water impermeable then. The pack 10 may come in various sizes for an arm, leg or shoulder. FIG. 7, to be applied, the pack 10 is held against the body part, i.e., wrist 24, and then bent around the wrist 24 forming a cuff such as shown in FIG. 7. This would be also done on the shoulder and since the bendable rods will remain bent, the bent pack 10 will loosely grip the shoulder, but additional compression may be used or available. The pack 10 may tightly enclose a portion of the body part, and thus be sufficiently in contact with the skin to provide appropriate thermal treatment. The use of straps would not be required. Although the pack 10 is best used on inactive body parts, it can be also used in active movement. The bendable rods may be on all four sides. The corner devices of the pack may be rounded. This product may be ideal for baby boomers, athletes, elderly with limited motion, and out-of-shape customers.

Figure 8:
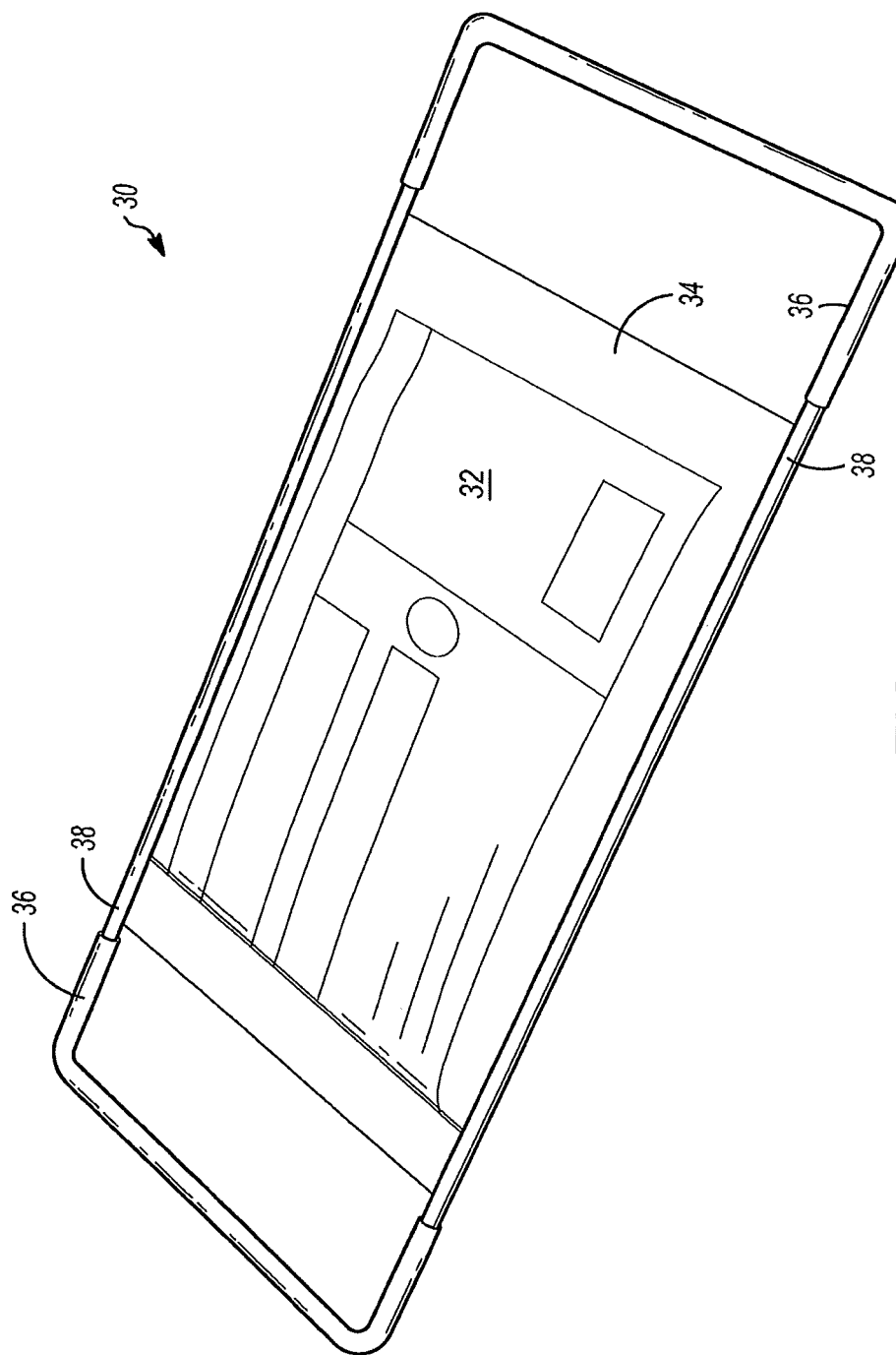
FIG. 8 shows the thermal treatment source with the heat source integrated into the pouch and further having handles thereon attached to the flexible rods
Figure 10:
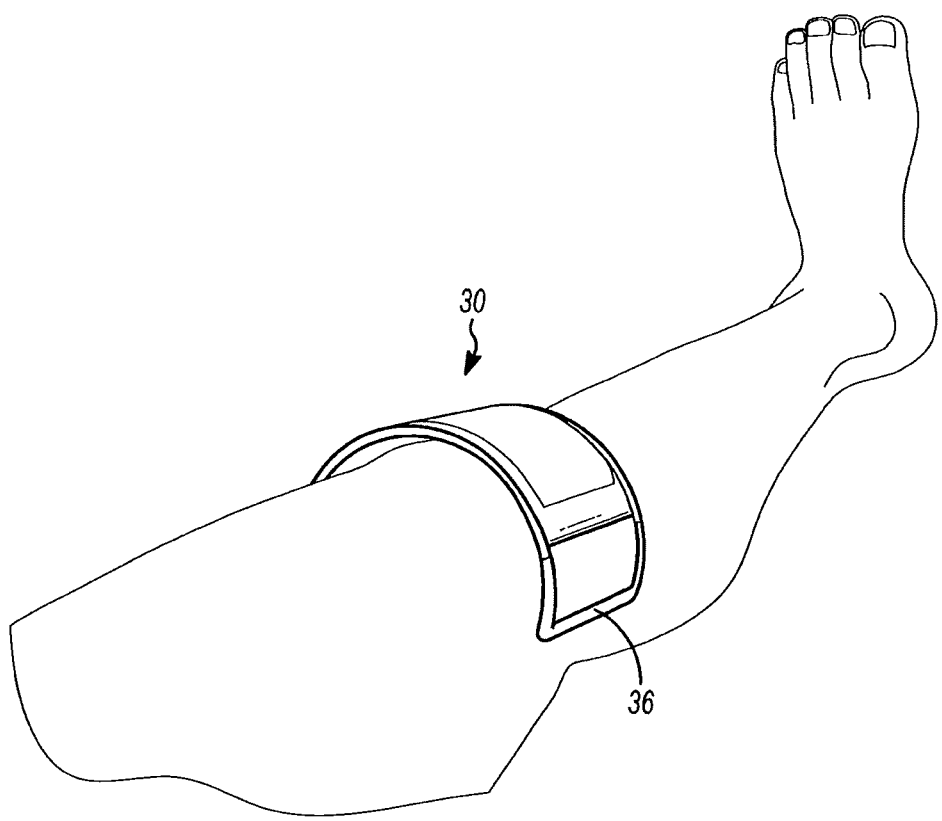
FIG. 10 shows the thermal treatment pack of FIG. 8 applied to a lower leg section with the handles gripping the leg.
Figure 11:
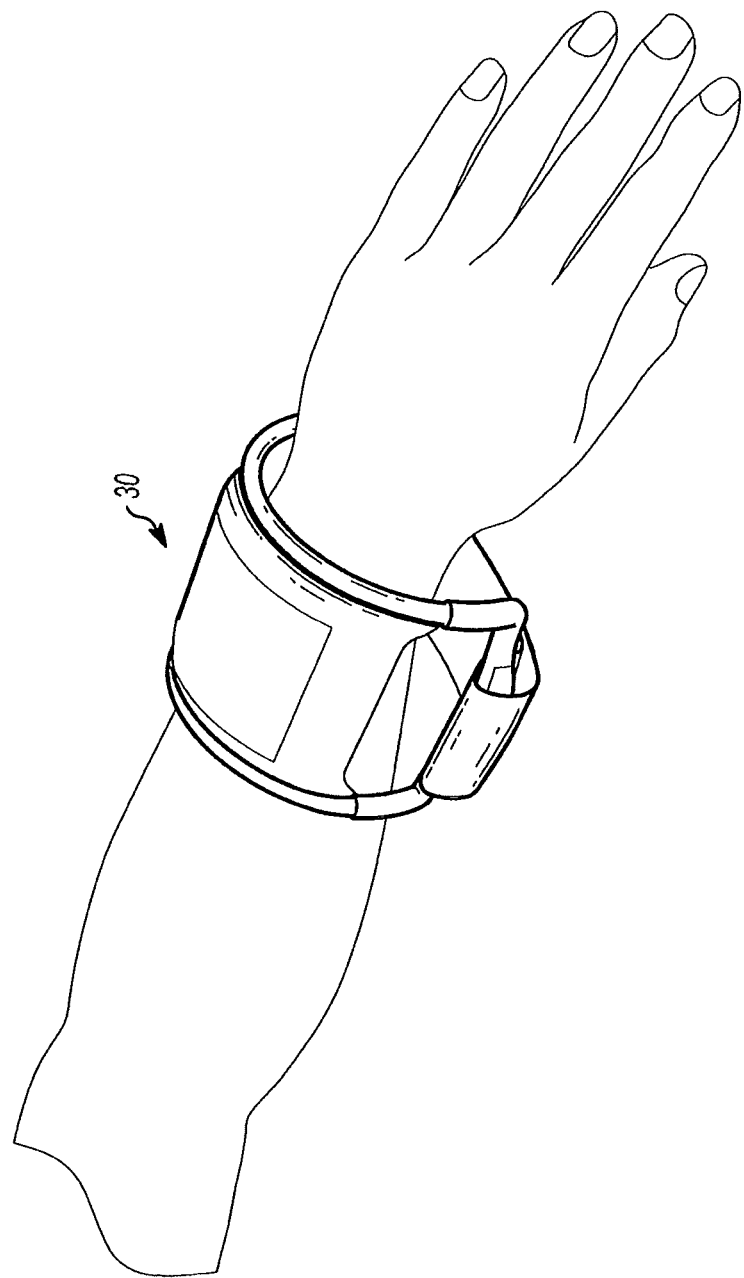
FIG. 11 shows the thermal treatment pack of FIG. 8 applied to a wrist by use of straps in the handles.

In another embodiment, FIG. 8 shows a thermal pack 30 with a thermal source 32 integrated into a pouch 34 and further having handles 36 thereon attached to the flexible, deformable and bendable rods 38 that provide a support frame. The handles 36 may be removed from the bendable rods 38, but can otherwise aid in the placement of the pack 30. The thermal source 32/pouch 30 is rectangular in shape and made of plastic-like material which would be waterproof. The thermal source 32 may be reusable by placing in a refrigerator or a microwave or a one-time use of heating or cooling material therein. The handles 36 provide a further reach about a body part that may have an irregular shape and may also be made of flexible, bendable rods like used in tie-wraps. The handles 36 shown are U-shaped. See FIGS. 14 to 17. FIG. 10 shows the thermal treatment pack 30 of FIG. 8 applied to a lower leg section, and FIG. 11 shows the thermal treatment pack 30 of FIG. 8 applied to a wrist.

Figure 9:
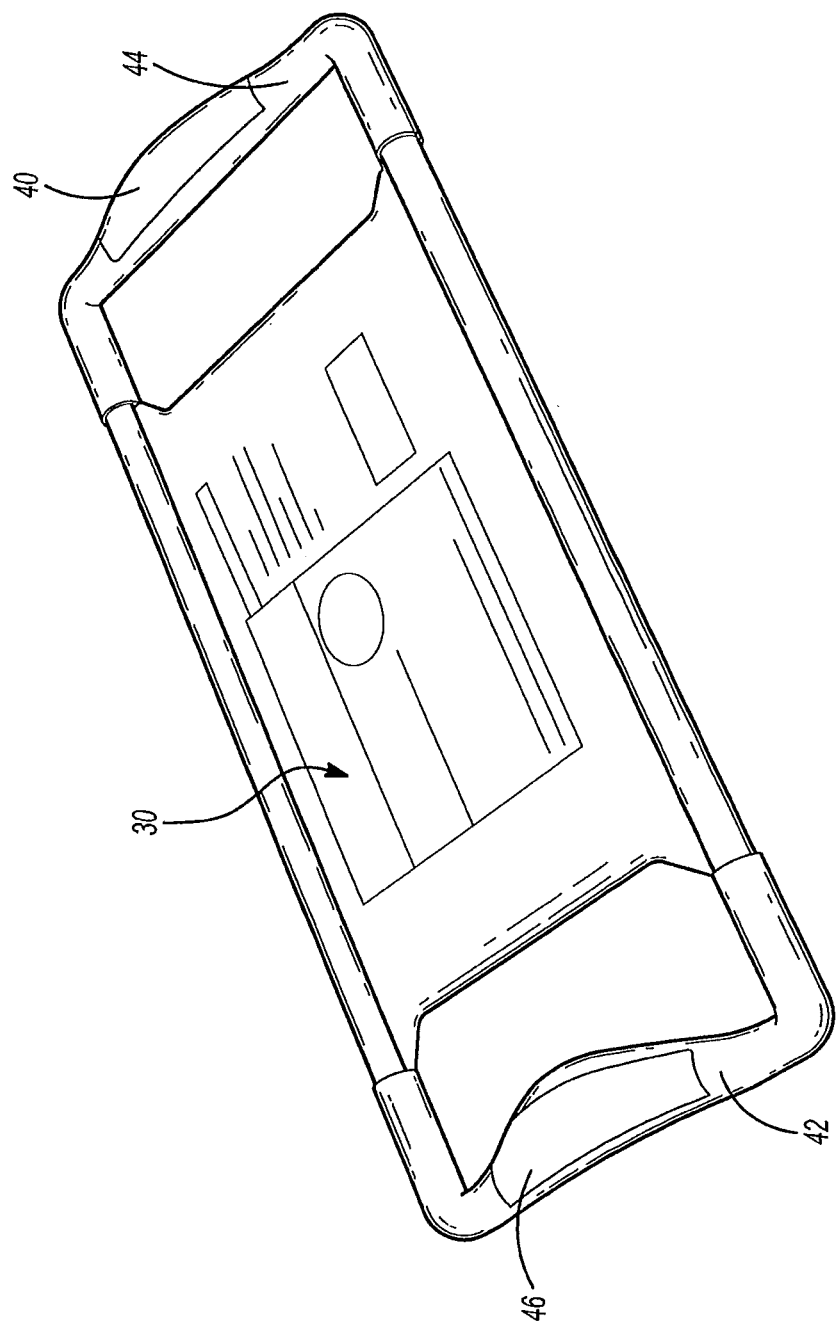
FIG. 9 shows alternative handles on the heat thermal treatment pack.
Figure 12:
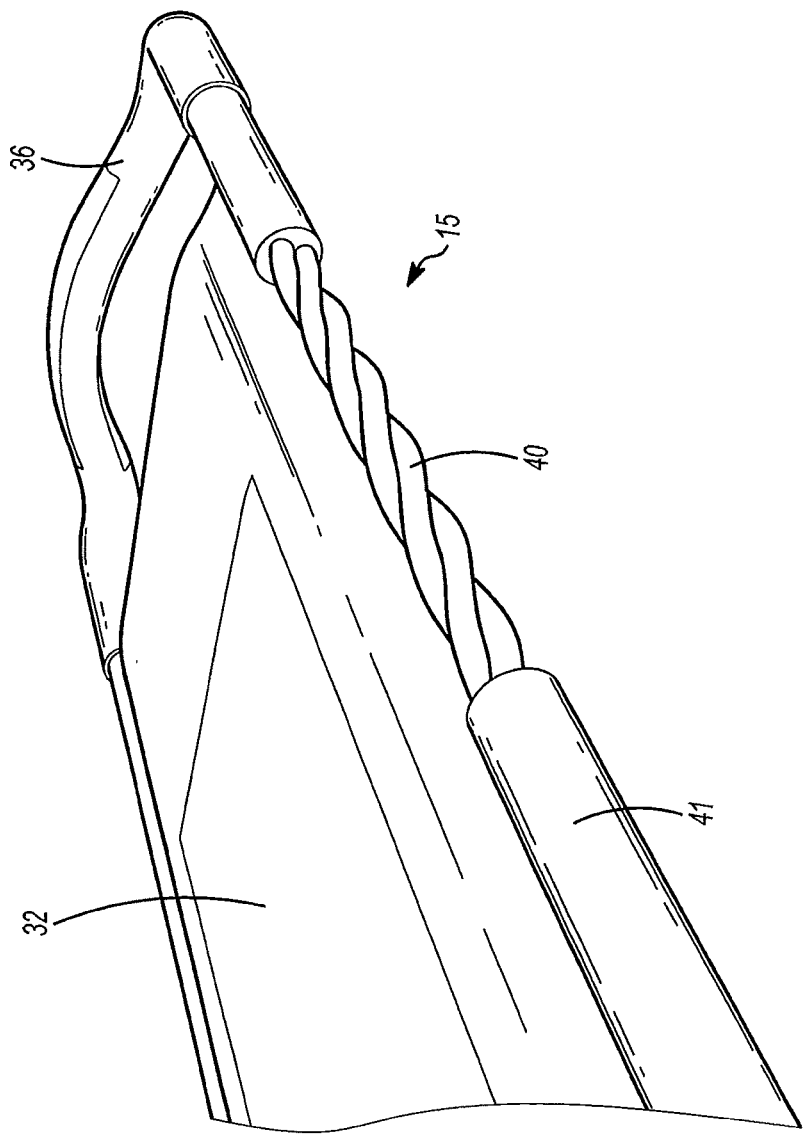
FIG. 12 shows partially a twisted wire as the frame with a foam cover supporting the thermal source.
Figure 13:
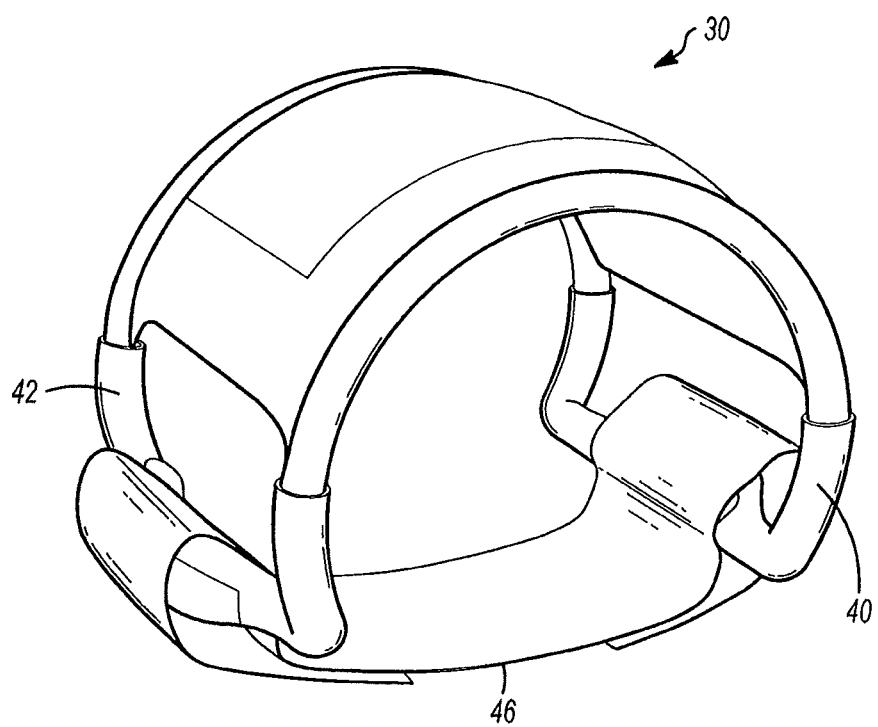
FIG. 13 shows a strap secured about the handles of the thermal treatment pack like that of FIG. 11 applied to a wrist.

FIG. 9 shows alternative handles 40 and 42 on the thermal treatment pack 30. The alternative handles 40 and 42 may have flattened sections 44 and 46, either being oriented perpendicular or parallel to the pouch. This provides for ease of handling and also for attachment of a strap 46 as shown in FIGS. 11, 12, and 13. With the use of a strap 46, the pack 30 can even be used on an active person.

Figure 3:
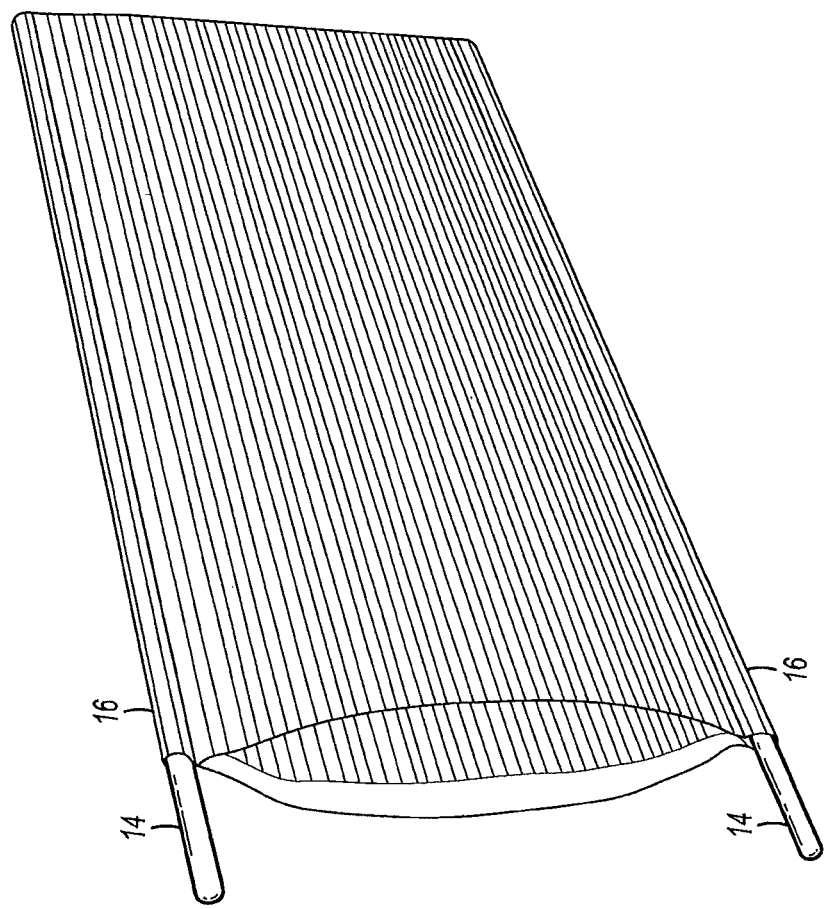
FIG. 3 is a perspective view of the thermal treatment pack as the flexible rods are being inserted of the present invention.
Figure 4:
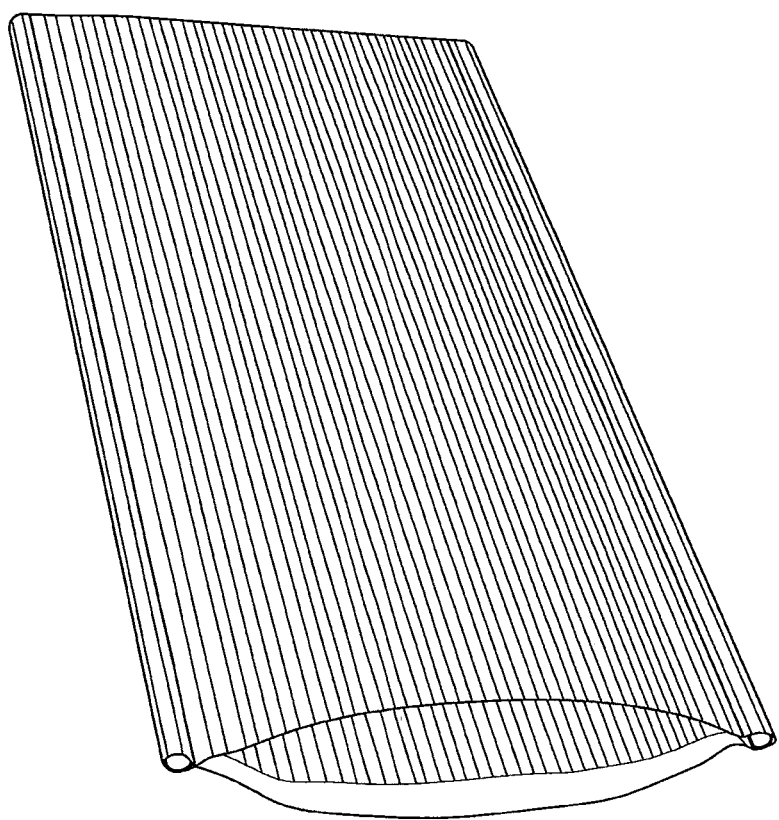
FIG. 4 shows the thermal treatment pack before the insertion of the heat source of the present invention.
Figure 5:
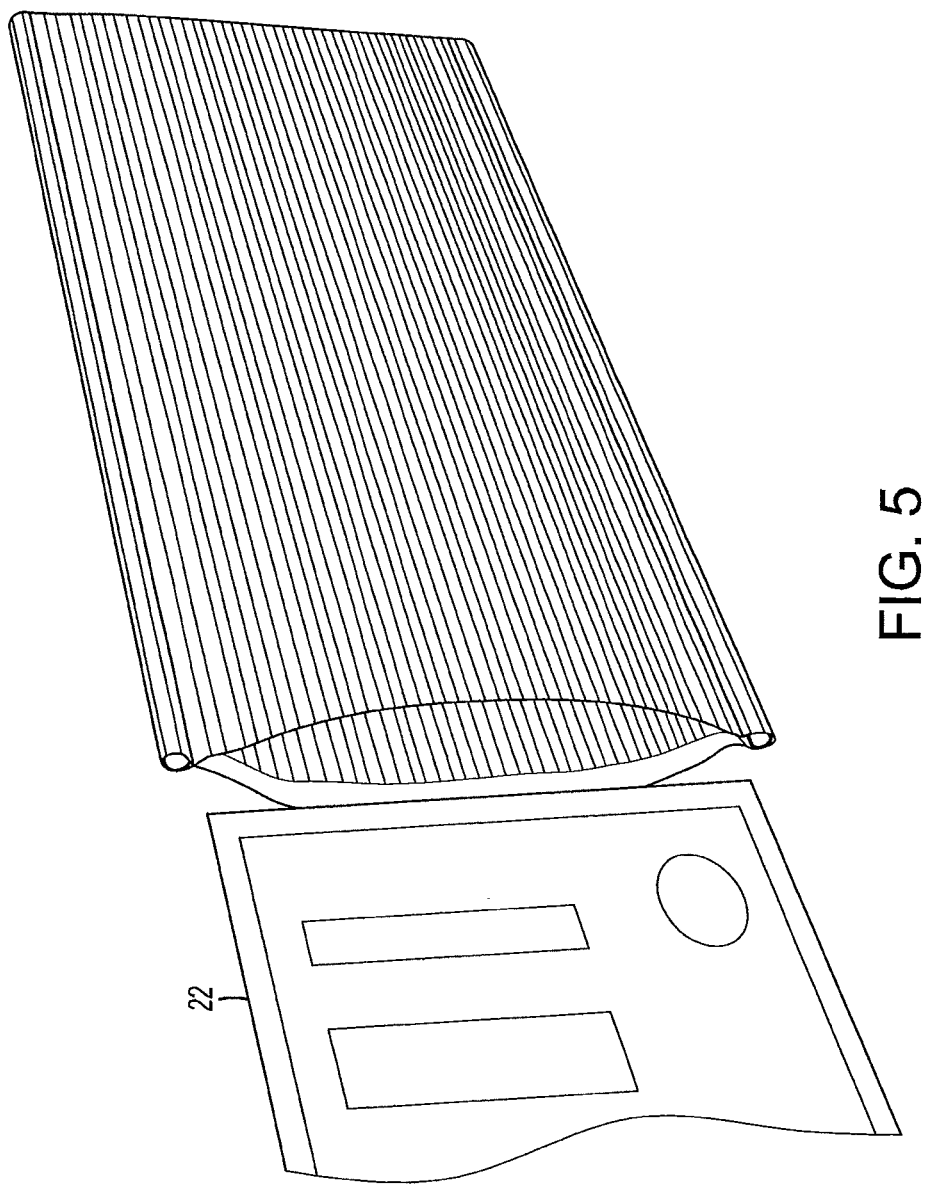
FIG. 5 shows the heat source being inserted into the pouch of the thermal treatment pack.
Figure 6:
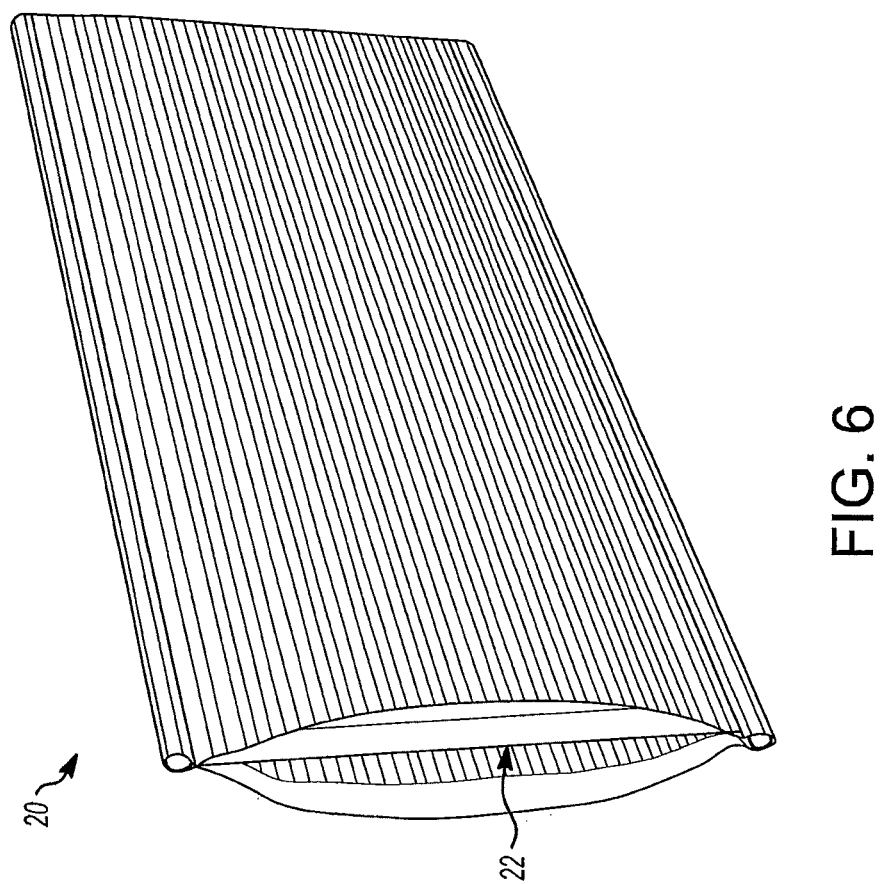
FIG. 6 shows the heat source within the pouch of FIG. 5.

Referring to FIGS. 2 and 3, the bendable or flexible or deformable rods 14 are like tie wraps. They are flexible, i.e., can be bent to a particular shape and will remain in that shape until bent further, and will resist bending to a certain degree. The may be made of a foam rod thereabout with the twisted wires therein. See FIG. 12. These bendable rods 38 may be of tubular shape as shown. The bendable rods 41, in FIG. 12, may be twisted wires 40 inside of a tube 41.

Figure 14:
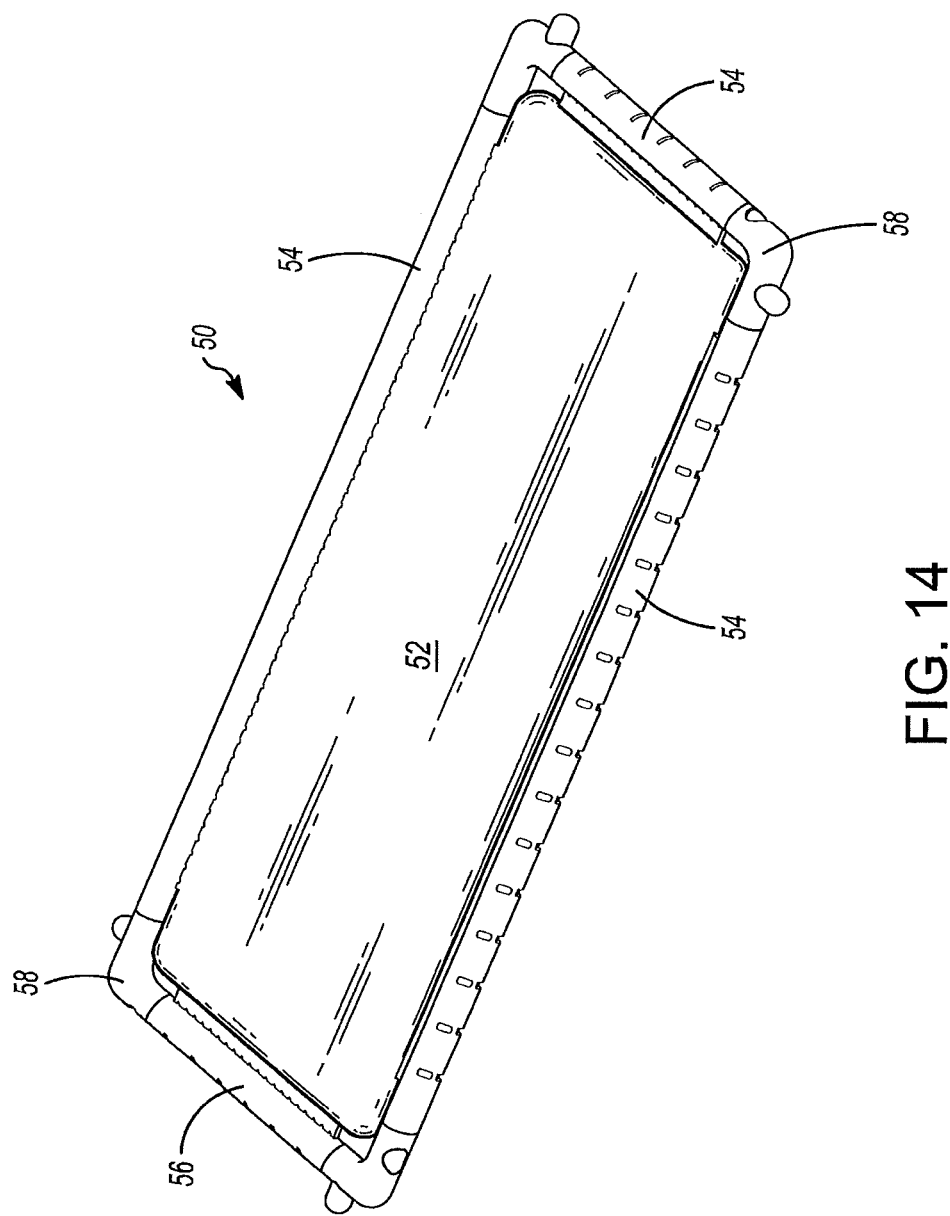
FIG. 14 shows a thermal treatment pack with the thermal source secured by bonding to the flexible rods thereabout.

Referring to FIGS. 14 to 17, in FIG. 14, a thermal treatment pack 50 is shown. A pouch 52 is designed to hold either cooling gel or heating gel or other material such as ice. The pouch 52 is plastic and is permanently and fixedly attached to two flexible side rods 54 being made of a foam material and having therein wires, not shown. Further, two end rods 56 are also flexible if used. The side rods 54 and end rods 56 may be jointed together by corner support devices 58 that are typically rounded.

Figure 15:
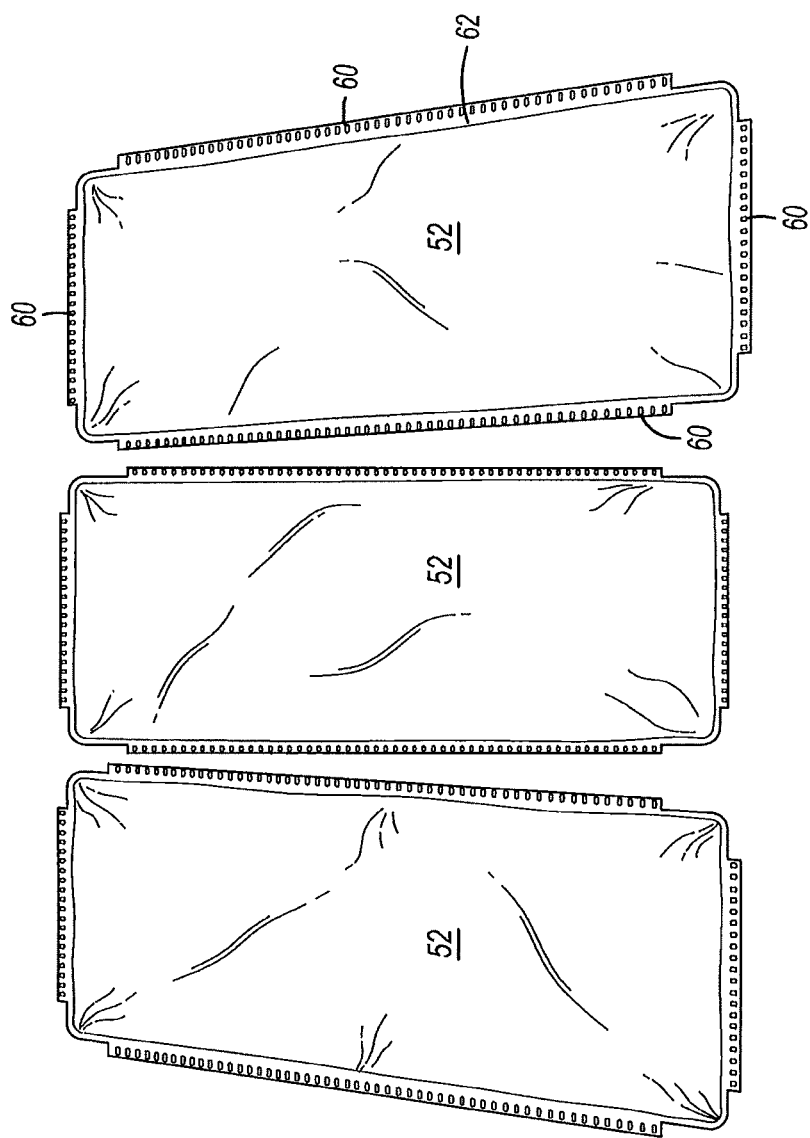
FIG. 15 shows the thermal source having edges for bonding to the flexible rods thereabout.

Referring to FIG. 15, the pouch 52 has extended edges 60 being made of similar material as the pouch 52. The pouch 52 may be about 3 to 4 inches wide and 6 inches long. Other sizes may be used since it may be used on a leg having a larger diameter than a wrist. The extended edges 60 extend therefrom by about ¼ to ½ inch and has a plurality of slotted holes 62 running along the length. In the embodiment of FIG. 14, both the sides and the ends of the pouch have this extended edge 60 thereon.

Figure 16:
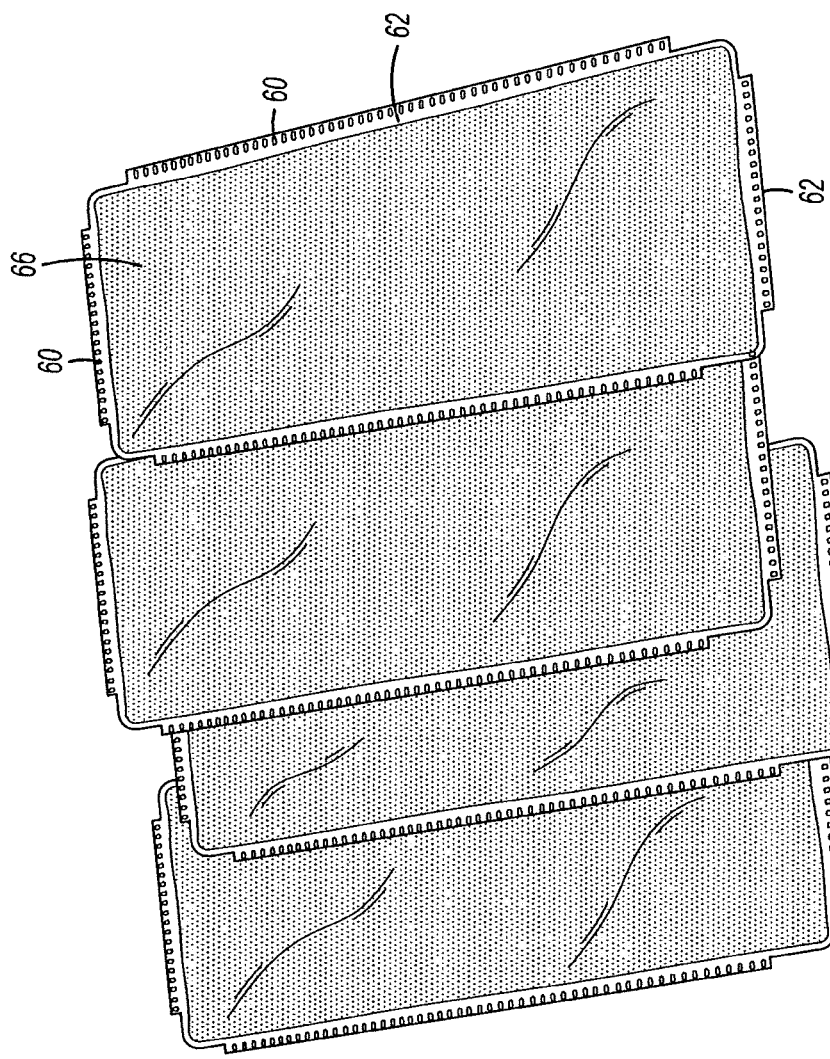
FIG. 16 shows thermal sources being gel packs having edge for bonding to the flexible rods thereabout.

These extended edges 60 used an vulcanization process to secure the edges 60 to the gel pack 52. The bendable rods 54/56 were enclosed in a foam and then secured to the edges 60 by ultrasonic welding. The pouches 52/60 have the extended edges of either the sides or the ends or both. The foam rods with corners are placed about the pouches 52/60. The pouch 52 shown in FIG. 14, being white, can hold material that maybe activated to provide heat. Referring to FIG. 16, a pouch 66 shown may be blue in color and filled with cold gel that may be placed in a refrigerator for cooling. Similar edges 60 having a slotted pattern thereon allow for secure attachment to the foam rods by vulcanization.

To cover a large area, the pack 50 may be attached to similar packs 50 by use of snap fittings as shown in FIG. 14. Each side of the pack 50 has a male snap fitting 90 and a female snap fitting 92. The opposite snap fittings are attached to each corner devices 58 and when constructed the other adjacent side has the snap fittings reversed so that one pack 50 may be pushed into an adjacent pack 50.

FIGS. 17A, 17B and 17C illustrate a pack 80 assembled and disassembled showing the various items thereon.

Figure 18A:
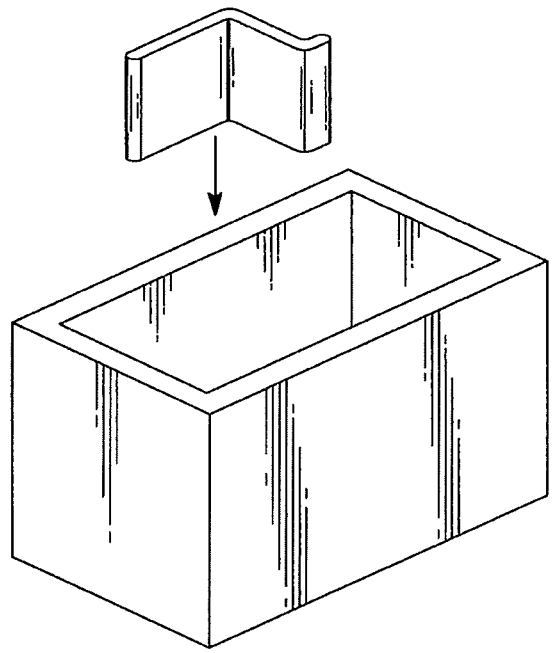
FIG. 18A show the pack being bent and before placement in a container such as a cooler.
Figure 18B:
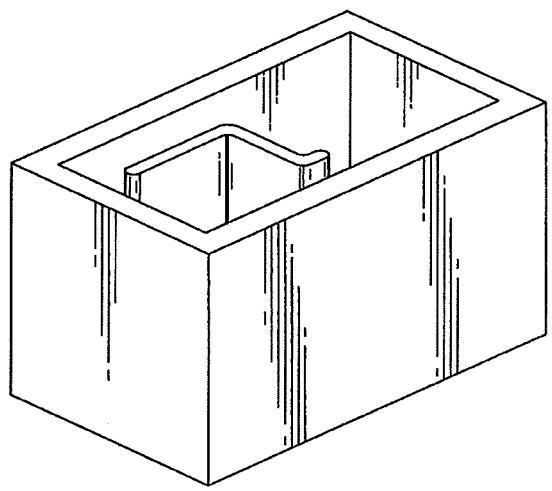
FIG. 18B shows the bent pack inside of a container.

In a further embodiment as shown in FIGS. 18A and 18B, the thermal pack 61 if a cold pouch with gel material or ice therein, may be used in food storage and allows for molding or shaping of the pack 61 to more closely fit about food items, not shown, in a container 62.

Figure 19:
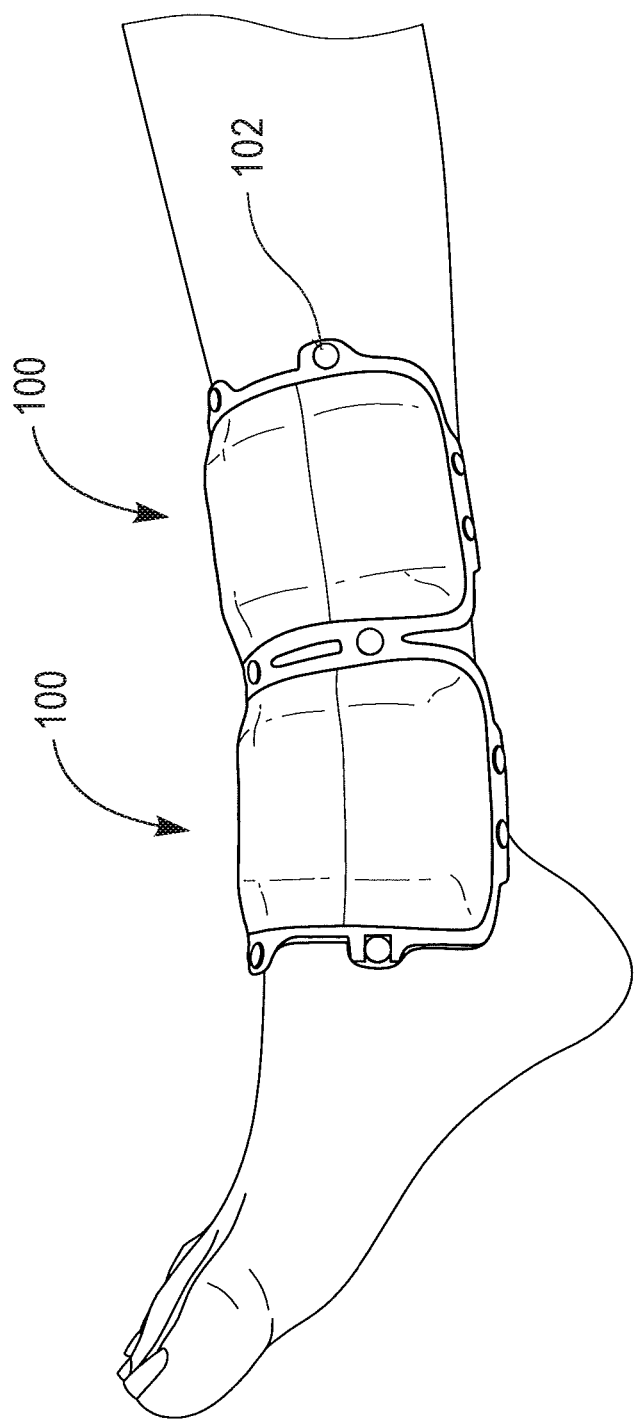
FIG. 19 illustrates a configuration of two thermal packs connected together and used on an ankle region of a user.
Figure 20:
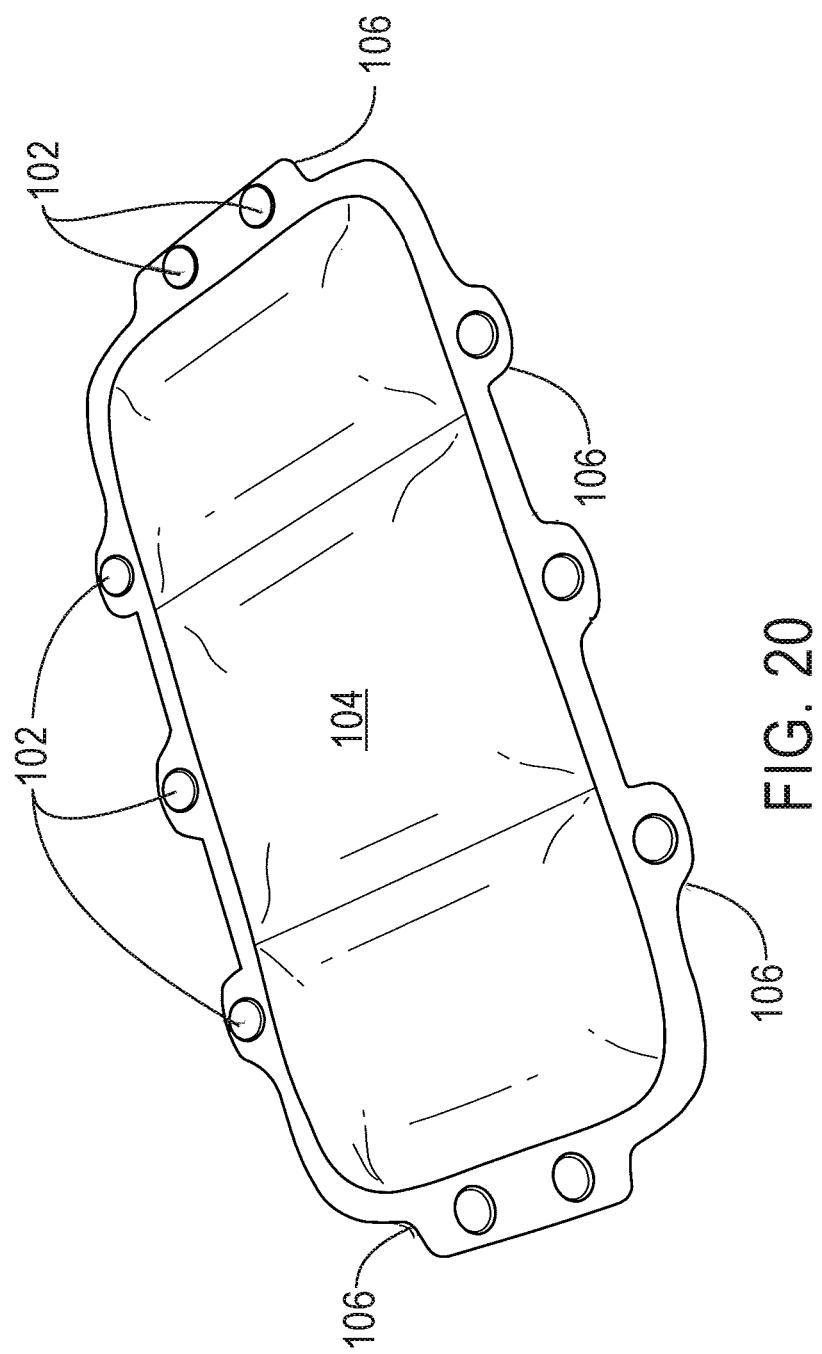
FIG. 20 illustrates a thermal pack from the two thermal packs illustrated in FIG. 1.

Referring now to FIGS. 19 and 20, there is shown a thermal pack as described above. FIG. 20 shows one such thermal pack 100, while FIG. 19 shows two thermal packs 100 attached together with connectors, such as snaps 102, where the two thermal packs 100 are formed to conform to a shape of an ankle area of a user. The snaps 102 can be configured as those known in the art, such as those used on canvas boat covers, having a male part and a female part which mate together when the male part is pressed into the female part and which can be separated with the application of a force separating the male part from the female part. FIGS. 19 and 20 illustrate the snaps 102 being spaced longitudinally on each of the four sides of the thermal pack 100. The snaps 102 can be providing on only one side, two sides or three sides and can be spaced in any intervals and provided in any number, including a single snap 102. The snaps 102 can be disposed on a pouch projection 106 in a one-to-one correspondence or two or more-to-one correspondence. The snaps 102 can be formed of metal or plastic. Plastic snaps being capable of being used in a microwave where the thermal material in the pouch is being heated in a microwave.

The thermal pack 100 includes a pouch 104 containing a thermal source in a cavity formed by two sides of the pouch 104. The thermal source can be either heated or cooled to apply either hot or cold, respectively, to the ankle area or other body area. Some materials are capable of being both heated and cooled, thereby allowing the thermal pack 100 to be used for application of both heat and cold to a body part of the user. The pouch 104 is formed of materials, such as neoprene and canvas. While all portions of the pouch 104 can be the same material, more than one material can be used to form the pouch 104. For example, one side of the pouch 104 can be a first material, such as neoprene and another side of the pouch 104 can be a second material, such as canvas.

A bendable and deformable support (not shown in FIGS. 19 and 20) that is either attached to or disposed within the pouch 104 is provided such that the pouch 104 can be deformed into a shape matching a contour of a body part and the pouch is maintained in the shape while applied to the body part by the bendable and deformable support frame. Although the bendable and deformable support frame can be provided on all sides of the thermal pack, the bendable and deformable support frame can be providing on only a single side or only on two opposing sides. Still further, the bendable and deformable support frame can be providing interior to the pouch. The bendable and deformable support frame can be a single or plurality of twisted wires formed of a metal material having the desired properties of being capable of being deformed into a shape matching a contour of a body part and allowing the pouch to be maintained in the shape while applied to the body part by the bendable and deformable support frame. The wire or plurality of twisted wires can be encased in an elastomer/resin casing so as to be safe to microwave in the case where the bendable and deformable support frame is fixed to the pouch and the thermal material is heated in the microwave.

Figure 21:
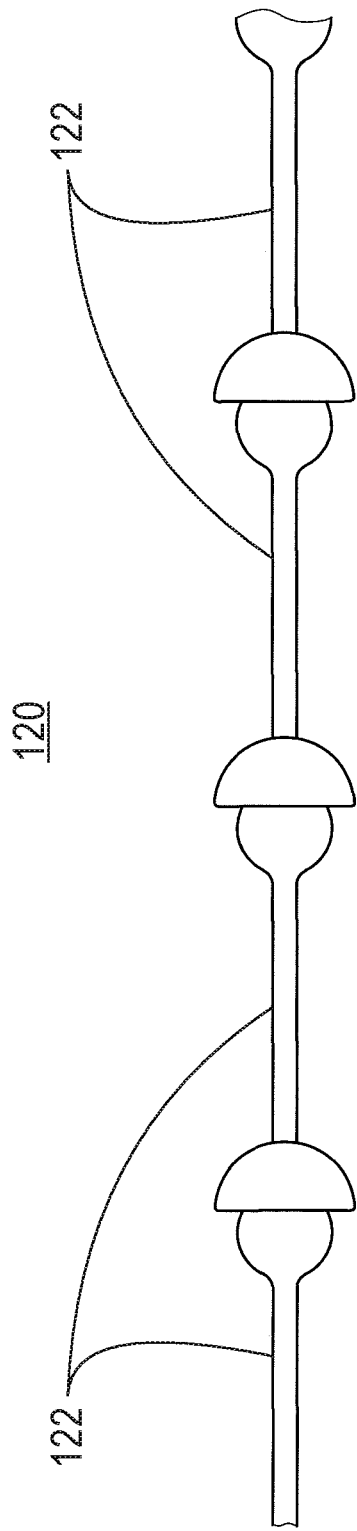
FIG. 21 illustrates an embodiment of an elongated bendable member for use in the thermal packs.
Figure 22:
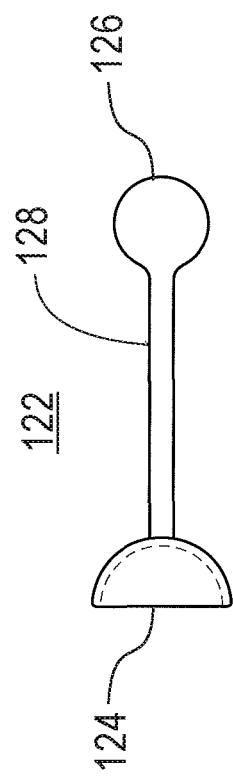
FIG. 22 illustrates a cup and ball rod component of the elongated bendable member of FIG. 21.

FIGS. 21 and 22 illustrate another embodiment of the bendable support frame in the form of an elongated member 120 having the same properties as a wire in that the elongated member 120 is capable of being deformed into a shape matching a contour of a body part and allowing the pouch to be maintained in the shape while applied to the body part. The elongated member 120 comprises a series of cup and ball members 122. Each cup and ball member 122 includes a cup 124 and ball 126 at each end of a shaft 128. The ball 126 of each cup and ball member 122 fits into a cup 124 of an adjacent cup and ball member 122 such that the ball 126 rotates in the cup 124 in a way to achieve the desired properties discussed above. The ball and cup members 122 can be formed of a resin material and the elongated member 120 can be further covered with a covering, such as a heat shrink tubing, to enhance such properties.

Figure 23:
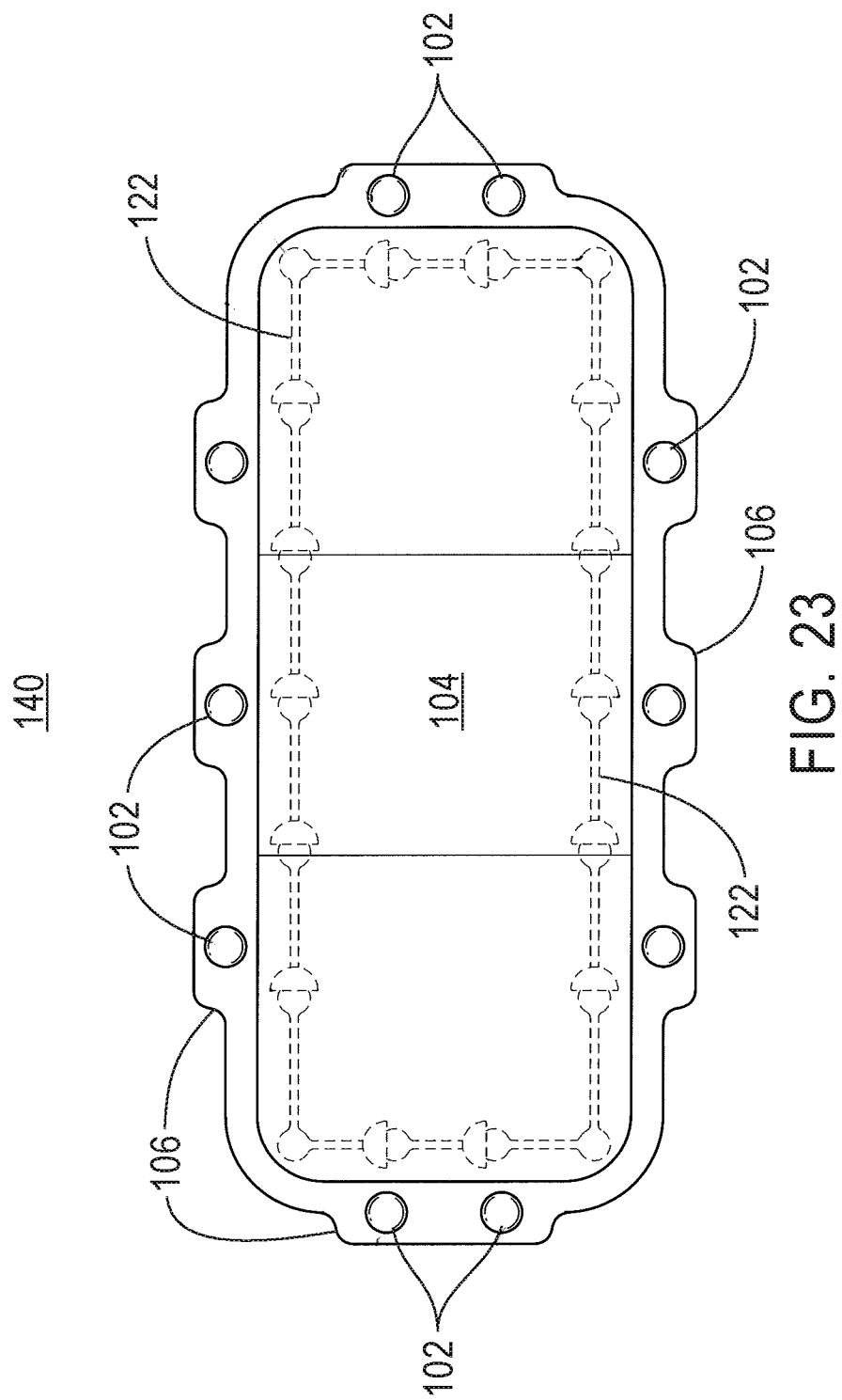
FIG. 23 illustrates a thermal pack employing the elongated bendable member of FIG. 21.

FIG. 23 illustrates an embodiment of thermal pack 140 similar to that of FIG. 20 with the exception that the elongated member 122 is disposed on all four sides of the pouch 104 and within the pouch 104. Alternatively, the elongated member 122 can be provided on less than all four sides and in an interior of the thermal pouch 104. Furthermore, the elongated member 122 can be disposed along an edge of the thermal pack 140 outside of a cavity formed in the pouch 104. Furthermore, the elongated member 122 can be removable from the pouch 104 or thermal pack 140.

Figure 24:
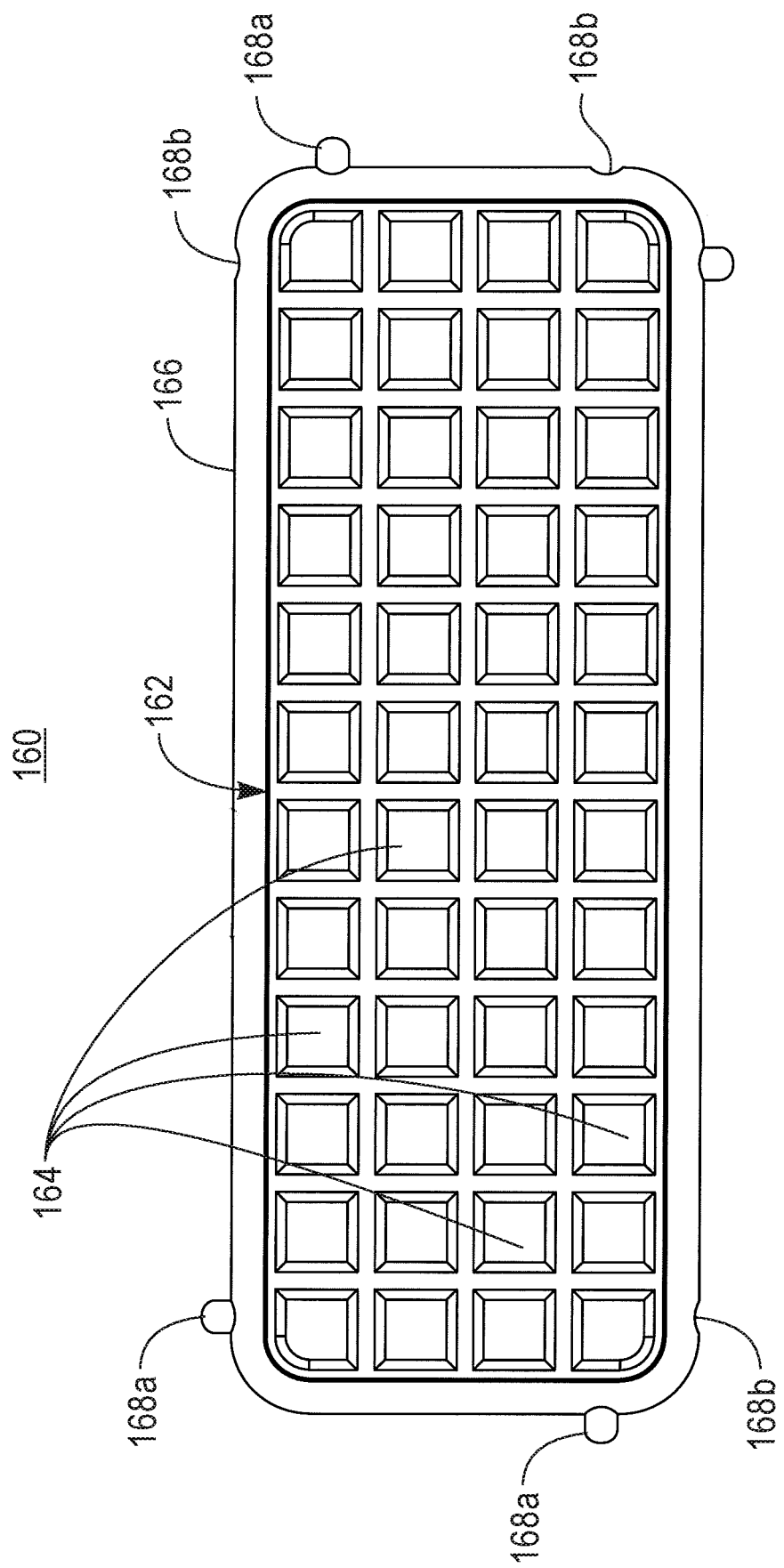
FIG. 24 illustrates another embodiment of a thermal pack.
Figure 25:
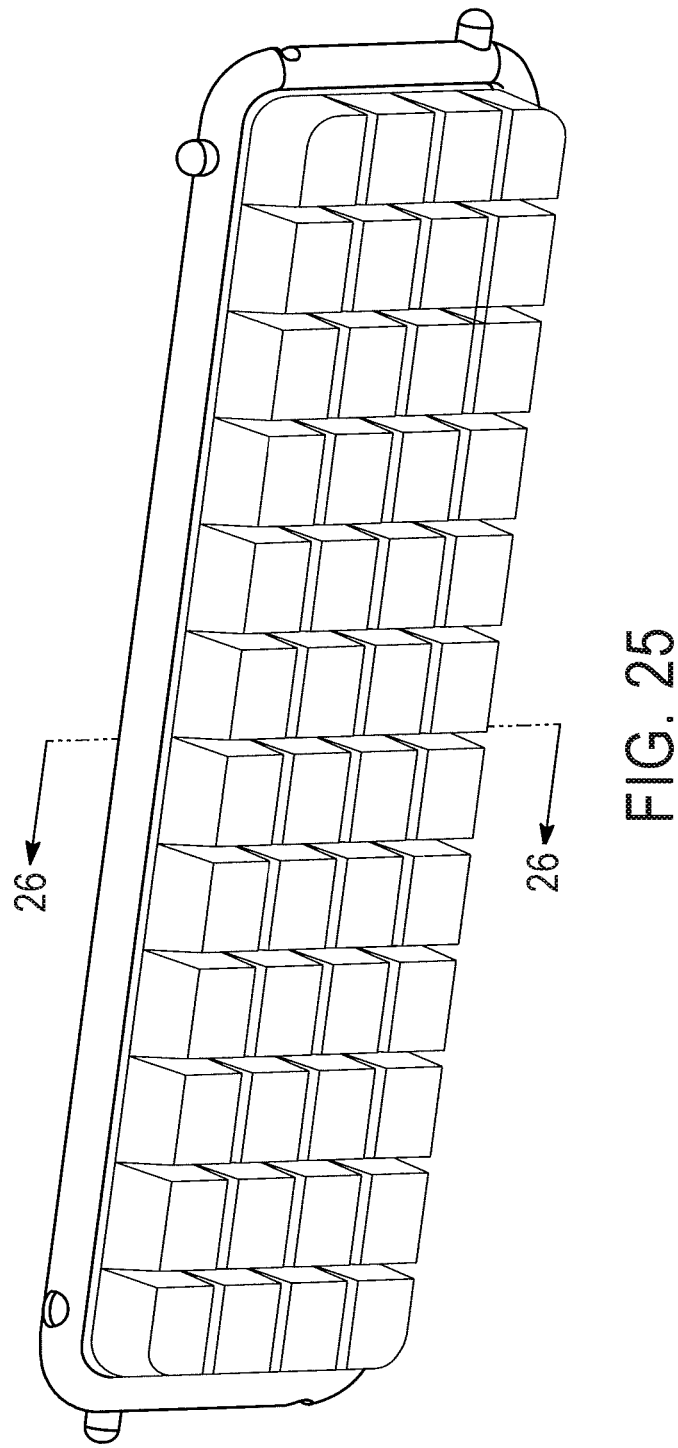
FIG. 25 illustrates a perspective view of the thermal pack of FIG. 24.
Figure 26:
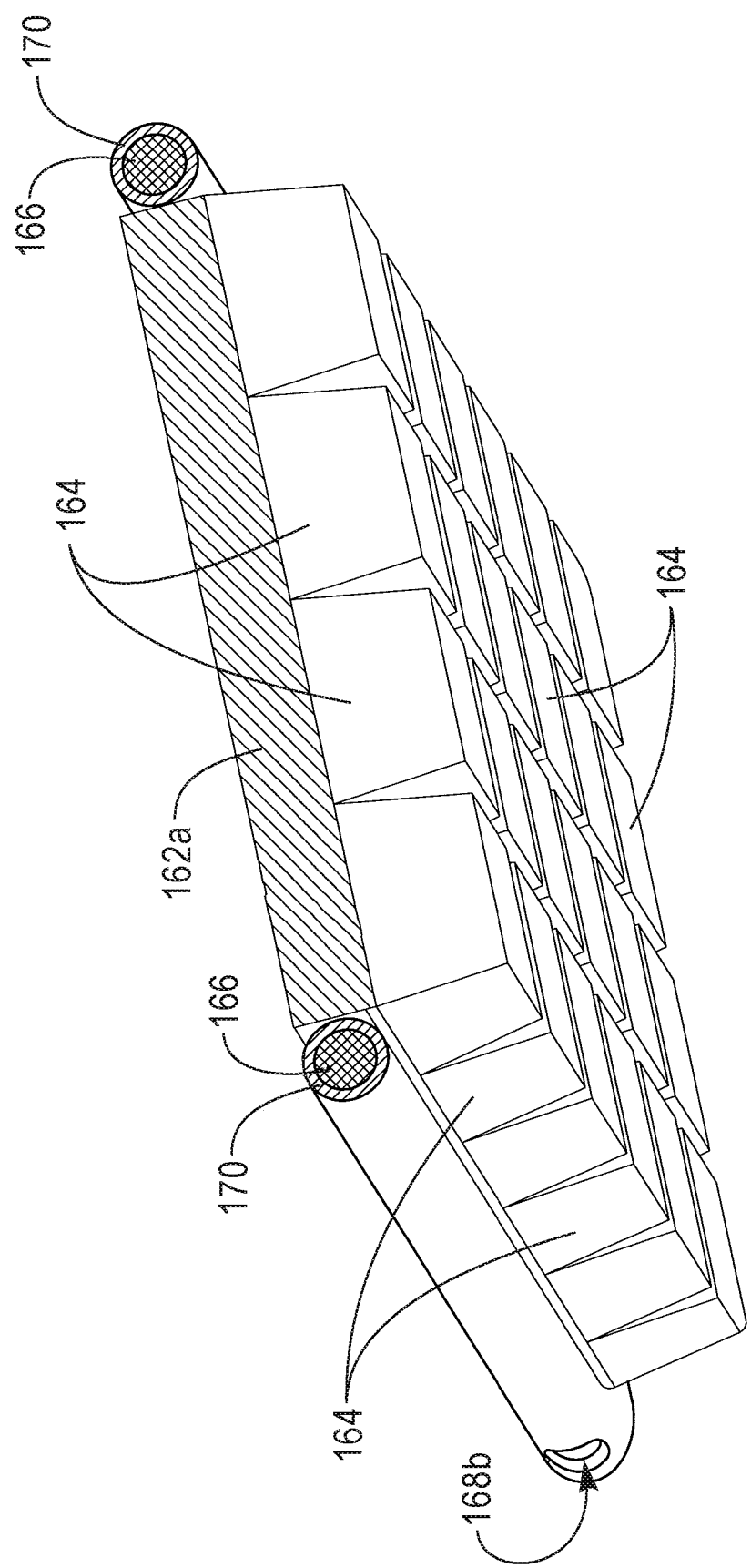
FIG. 26 illustrates a sectional view of the thermal pack of FIG. 25 as taken along line 26-26 in FIG. 25.

Referring now to FIGS. 24-26, there is shown another embodiment of a thermal pack 160 having a segmented pouch 162 formed of a plurality of pouch segments 164. The pouch segments 164 can be any shape or size and provided in any number greater than two. The thermal pack 160 of FIG. 24 illustrates a great number of small pouch segments 164 for increasing flexibility of the pouch and concentrating an amount of thermal material contained in each pouch segment 164.

The thermal pack 160 also includes a bendable and deformable support frame 166 provided at all four sides of the pouch 162 to outline the plurality of pouch segments 164. Male and female connectors 168a, 168b are also provided on a periphery of the thermal pack to allow similarly configured thermal packs to be connected together with the thermal pack 160. As shown in FIG. 26, the pouch 162 is formed having the thermal material in both a common portion 162a of the pouch 162 and in each of the pouch segments 164. Furthermore, the bendable and deformable support frame 166 is provided in a cavity 170 apart from the cavity forming the pouch 162.

Referring now to FIGS. 27 and 28, there are illustrated first and second thermal packs 180, 200 each having similar features to those described above with regard to any of FIGS. 20, 23 and 25. Thermal pack 180, although larger in size than thermal pack 200 has a similar connector (snaps 102) configuration and spacing such that the larger thermal pack 180 can be connected to the smaller thermal pack 200 to conform with irregular body surfaces, such as the shoulder area illustrated in FIG. 28.

Figure 29:
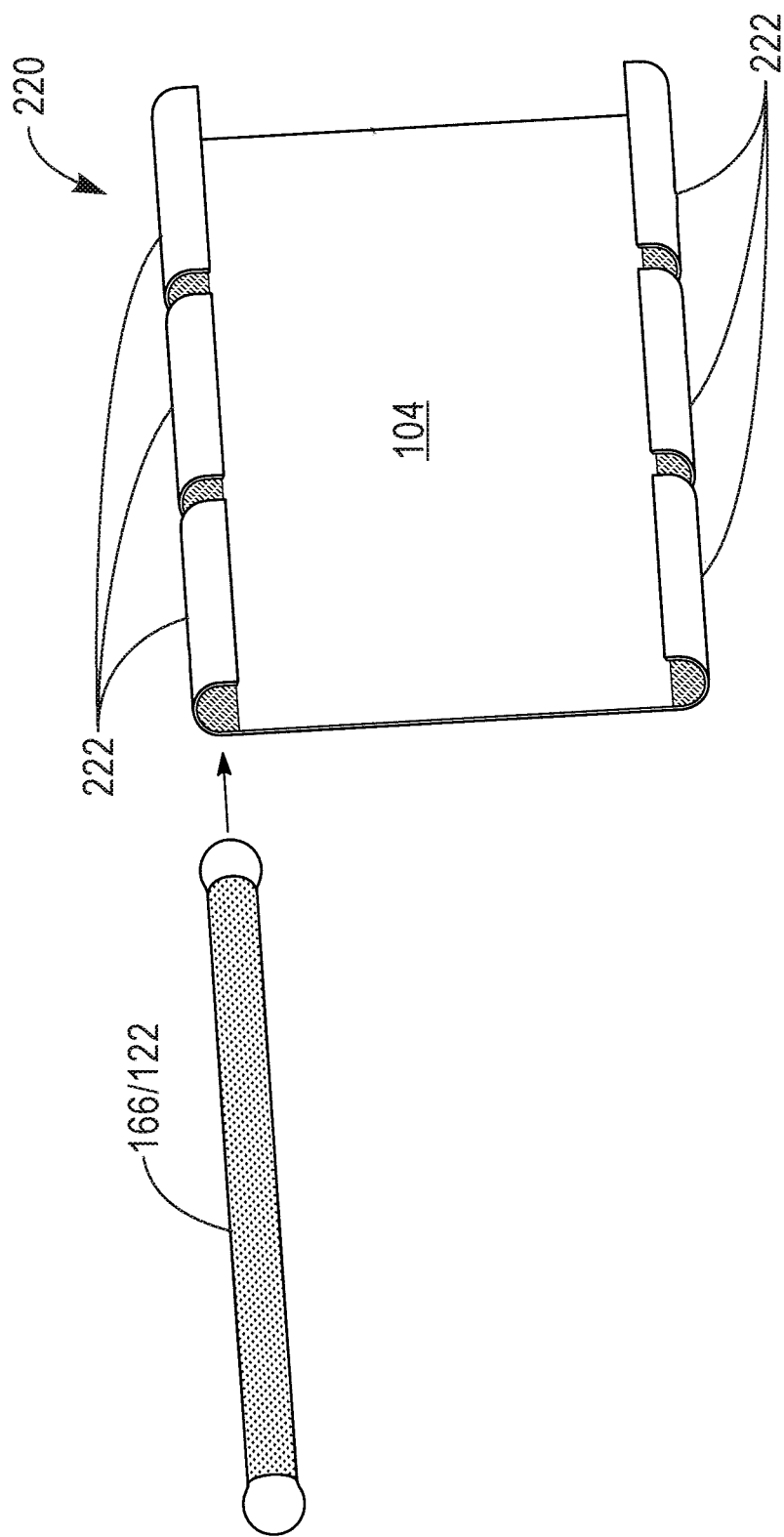
FIG. 29 illustrates another embodiment of a thermal pack having a removable bendable elongated wire.

Referring now to FIG. 29, there is shown schematically a thermal pack 220 having similar features to those described above with regard to any of FIGS. 20, 23 and 25. However, in the thermal pack 220 of FIG. 29, the bendable and deformable support frame 166 is removable from the pouch 104. In such configuration, the pouch has ends 222 which can secure the bendable and deformable support frame 166 to the pouch 104. Although an means of releasable securing known in the art can be employed to attach the bendable and deformable support frame 166 to the pouch 104, in the embodiment of FIG. 29, the bendable and deformable support frame 166 has one of a hook or loop fastener (e.g., Velcro™) and the pouch ends 222 has the other of the hook or loop fastener. Such configuration allows use of differently configured bendable and deformable support frame 166 and also allows use of metal components for the bendable and deformable support frame 166 which can be removed when microwaving where the thermal material in the pouch 104 is being heated.

Figure 30:
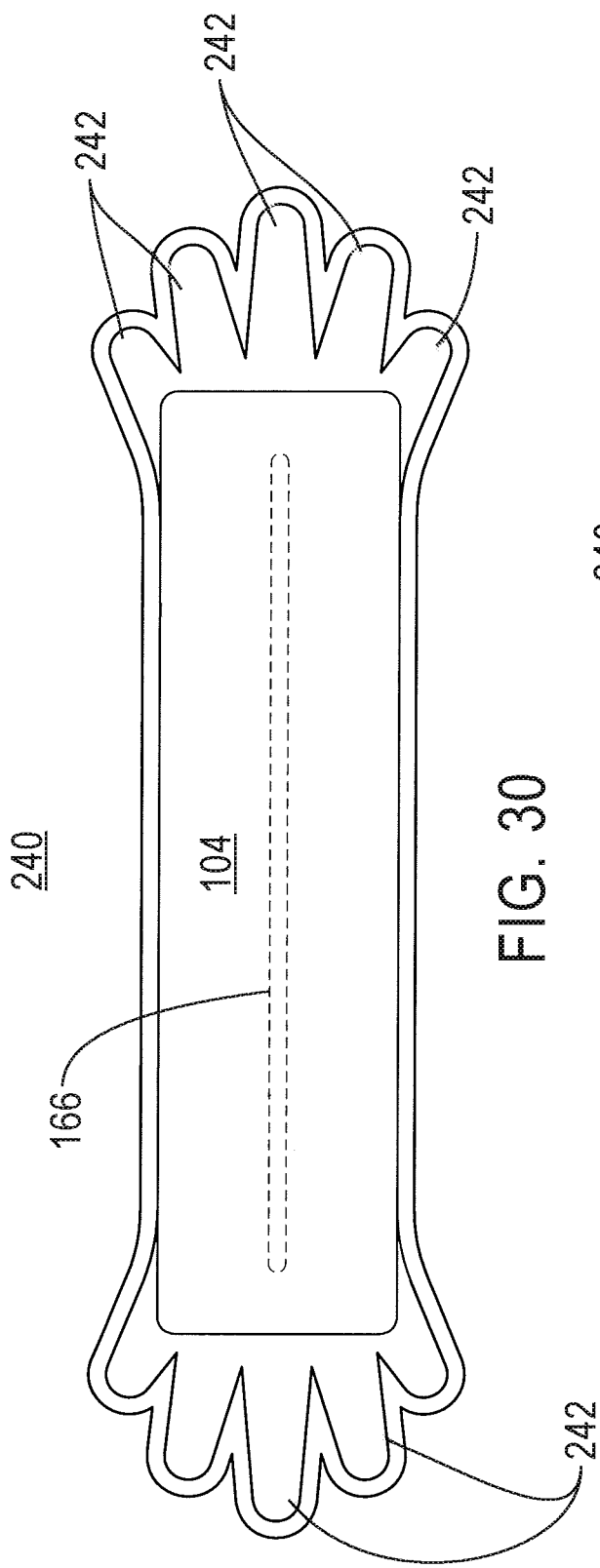
FIG. 30 illustrates another embodiment of a thermal pack having adhesion portions at ends thereof.
Figure 31:
FIG. 31 illustrates the thermal pack of FIG. 30 used on a head of an infant.

Turning next to FIGS. 30 and 31, there is shown another embodiment of thermal pack 240. The thermal pack 240 of FIGS. 30 and 31 can be configured in any of the ways disclosed in FIGS. 20, 23 and 25. However, in the thermal pack 240 of FIG. 30, the bendable and deformable support frame 166 is centrally located in the pouch 104. Furthermore, although the thermal pack 240 can be configured with connectors 102 for connecting the same to other similarly configured thermal packs, such connectors are not shown in FIG. 30. The thermal pack 240 of FIG. 30 includes one or more projections 242 extending from one or both ends of the thermal pack (FIG. 30 illustrates such projections 242 extending from both ends). The projections 242 include an adhesive for applying the thermal pack to a body part, such as a head of an infant, as shown in FIG. 31. The adhesive can be single or multiple use as is known in the art and can include a backing material that is peeled away to expose the adhesive for use.

Figure 32:
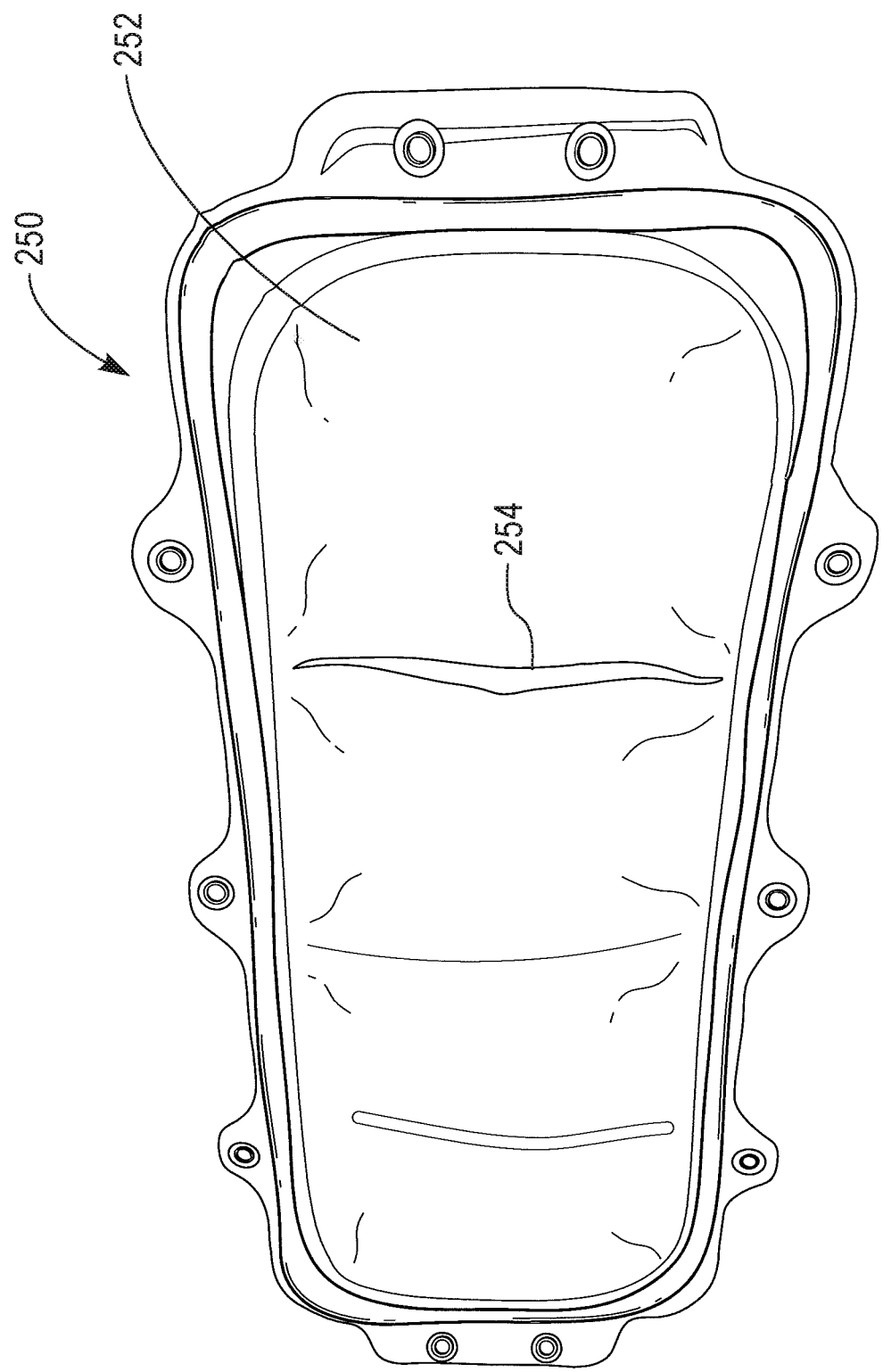
FIG. 32 illustrates another embodiment of a thermal pack having a slot for removing/inserting a secondary pouch having a thermal material.
Figure 33:
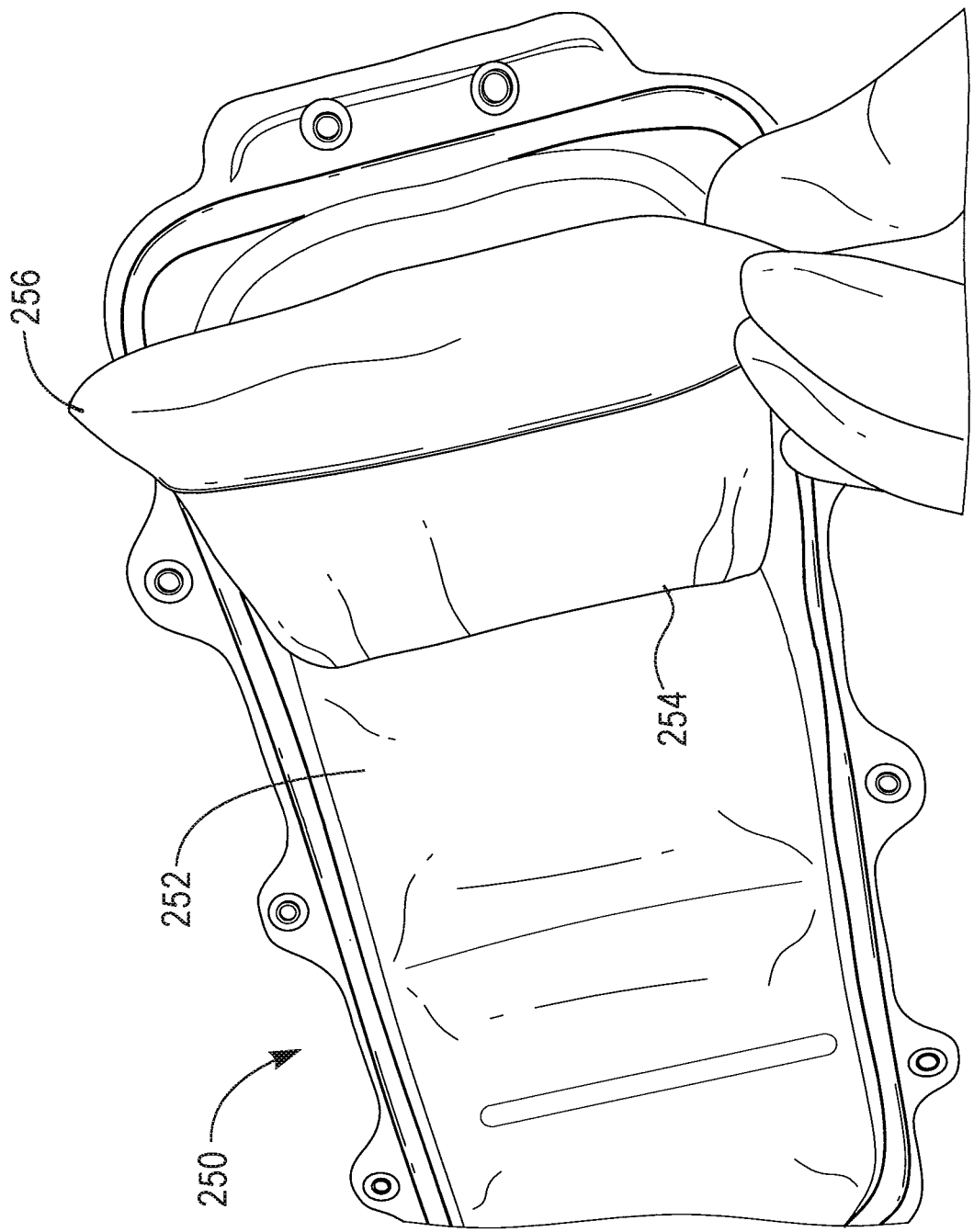
FIG. 33 illustrates the thermal pack of FIG. 32 in which the thermal material is being removed from the slot.

Turning next to FIGS. 32 and 33, there is illustrated another embodiment of a thermal pack, generally referred to by reference numeral 250. The thermal pack 250 can be configured as discussed above with regard to any of the above embodiments. However, the pouch 252 (a first pouch) of thermal pack 250 includes a slot 254 for accessing an interior of the pouch 252. The pouch 252 contains a second pouch 256 having the thermal material therein that can be inserted and/or removed through the slot 254. The second pouch 256 can be stored in a freezer or heated in a microwave and then inserted into the pouch 252 while in the cold or heated state.

Figure 34:
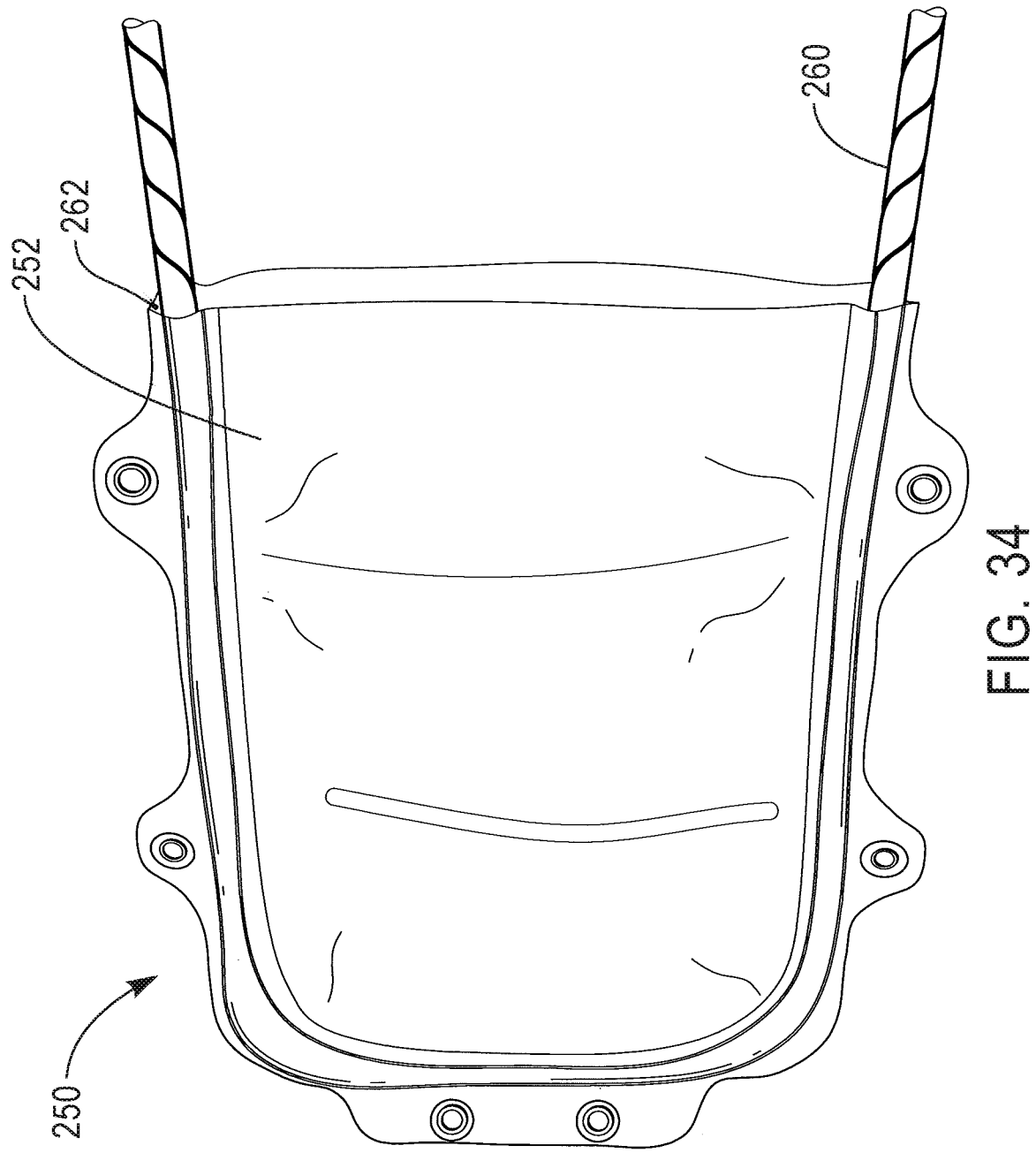
FIG. 34 illustrates a thermal pack having an embodiment of support frame.
Figure 35:
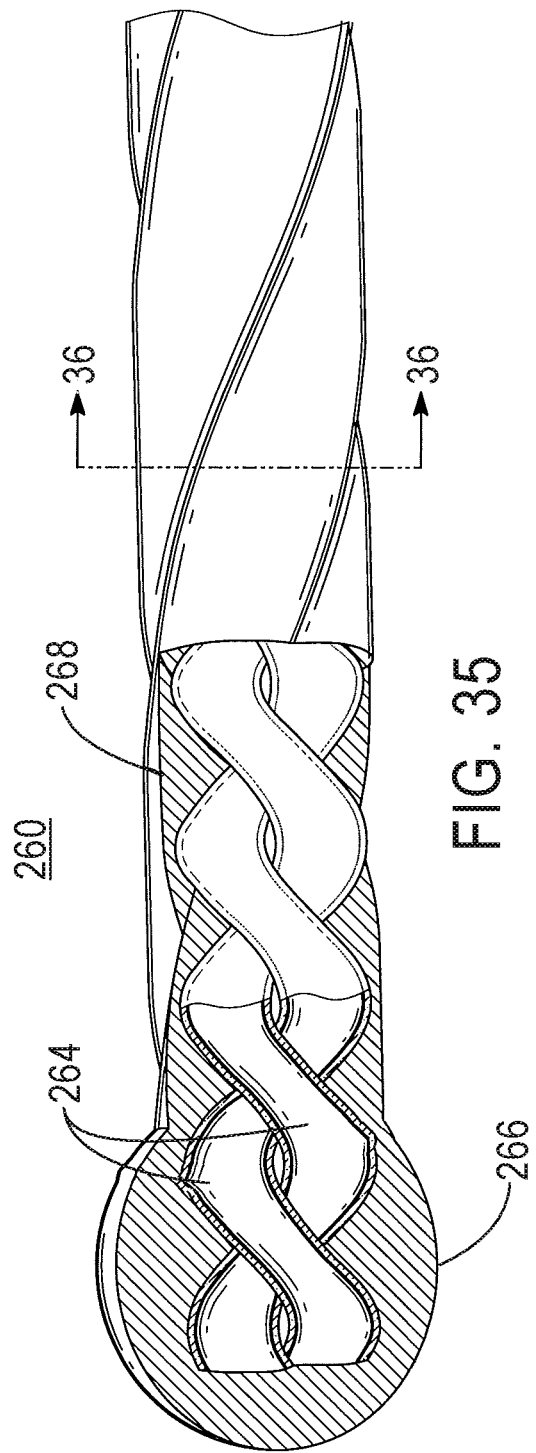
FIG. 35 illustrates a portion of the support frame of FIG. 34.
Figure 36:
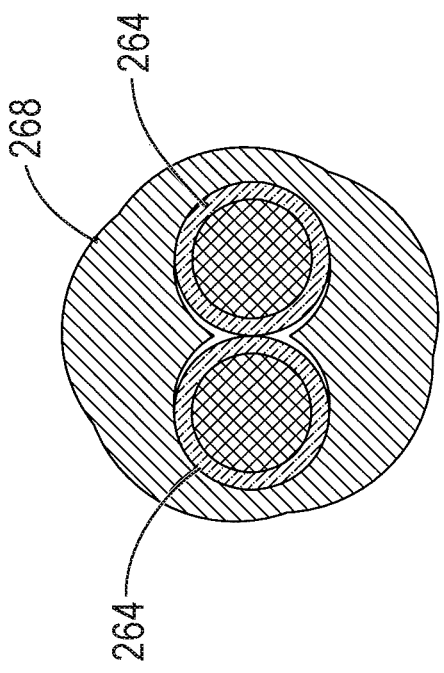
FIG. 36 illustrates a sectional view of the support frame of FIG. 35 as taken along line 36-36 in FIG. 35.

Turning now to FIGS. 34-36, the same illustrate an embodiment of a support frame/wire, generally referred to by reference number 260. FIG. 34 shows the support frame 260 for use with the thermal pack of FIG. 32, however, the support frame 260 can be used with any of the embodiments disclosed above, including that of FIG. 29. Although the support frame 260 is illustrated extending on all four sides of the pouch 252 in FIG. 34, the support frame 260 can extend on one, two or three sides. Furthermore, although the support frame 260 is shown being disposed in a cavity formed along the edges of the thermal pack 250, the support frame 260 can be releasable attached to the thermal pack 250, for example, as shown in FIG. 29.

As shown in FIGS. 35 and 36, the support frame/support wire can comprises one wire or a plurality of twisted wires 264 extending along the length of the support frame 260. The wire or plurality of twisted wires 264 are then encased in a resin or elastomer, such as a foam, such as a silicone foam material 268 into a predetermined shape. Such shape can have an elongated shape, as shown in FIG. 35. Such shape can also include a bulb 266 at an end thereof to prevent ends of the wires 264 from puncturing the material of the pouch 252 or cavity 262.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A thermal pack comprising: a cover defining a first pouch, the cover having a rectangular shape having two opposing first sides and two opposing second sides, where the two first sides are longer than the two second sides, the two first sides and the two second sides defining a peripheral edge of the cover and the two first sides and the two second sides further defining a body of the cover that extends inwardly from the peripheral edge, an outwardly extent of the body being defined by the peripheral edge, the peripheral edge being sealed to prevent access to the first pouch, the cover having a slot for accessing the first pouch from outside the cover, the slot being disposed in the body of the cover; a second pouch containing a thermal source and configured to be removable from and inserted into the first pouch through the slot; a bendable and deformable support disposed on at least each of the two first sides of the peripheral edge of the first pouch, the support being configured such that the cover is deformed into a shape matching a contour of a body part and the cover is maintained in the shape while applied to the body part by the support; one or more first connectors disposed along at least one of the two first sides of the peripheral edge of the first pouch for connecting the thermal pack to corresponding second connectors positioned on one or more other thermal packs.

2. The thermal pack of claim 1, wherein the cover has an extension projecting from the at least one of the two first sides of the peripheral edge of the first pouch, the one or more connectors being disposed on the extension.

3. The thermal pack of claim 1, further comprising the other thermal pack, wherein a spacing of the first connectors is the same as a spacing of the second connectors.

4. The thermal pack of claim 1, wherein the one or more first connectors are further disposed along each of the second sides of the peripheral edge of the first pouch.

5. A thermal pack comprising: a cover defining a first pouch, the cover having a rectangular shape having two opposing first sides and two opposing second sides, where the two first sides are longer than the two second sides, the two first sides and the two second sides defining a peripheral edge of the cover and the two first sides and the two second sides further defining a body of the cover that extends inwardly from the peripheral edge, an outwardly extent of the body being defined by the peripheral edge, the peripheral edge being sealed to prevent access to the first pouch, the cover having a slot for accessing the first pouch from outside the cover, the slot being disposed in the body of the cover; a second pouch containing a thermal source and configured to be removable from and inserted into the first pouch through the slot; a bendable and deformable support disposed on at least each of the two first sides of the peripheral edge of the first pouch, the support being configured such that the cover is deformed into a shape matching a contour of a body part and the cover is maintained in the shape while applied to the body part by the support; wherein the bendable and deformable support is further disposed on each of the second sides of the peripheral edge of the first pouch.

* * * * *